US008148398B2

(12) United States Patent
Savarese

(10) Patent No.: US 8,148,398 B2
(45) Date of Patent: Apr. 3, 2012

(54) INTERMEDIATE DURATION NEUROMUSCULAR BLOCKING AGENTS AND ANTAGONISTS THEREOF

(75) Inventor: John J. Savarese, Southbury, CT (US)

(73) Assignee: Cornell Research Foundation, Inc., Ithaca, NY (US)

(*) Notice: Subject to any disclaimer, the term of this patent is extended or adjusted under 35 U.S.C. 154(b) by 911 days.

(21) Appl. No.: 11/951,114

(22) Filed: Dec. 5, 2007

(65) Prior Publication Data

US 2008/0139482 A1 Jun. 12, 2008

Related U.S. Application Data

(60) Provisional application No. 60/873,132, filed on Dec. 6, 2006.

(51) Int. Cl.
*C07D 401/02* (2006.01)
*A61K 31/4725* (2006.01)

(52) U.S. Cl. ........................................ 514/308; 546/140

(58) Field of Classification Search ........................ None
See application file for complete search history.

(56) References Cited

U.S. PATENT DOCUMENTS

| | | | |
|---|---|---|---|
| 3,004,031 A | | 10/1961 | Taylor et al. |
| 4,036,959 A | | 7/1977 | Green et al. |
| 4,039,682 A | * | 8/1977 | Ausman et al. |
| 4,179,507 A | | 12/1979 | Stenlake et al. |
| 4,192,877 A | | 3/1980 | Savarese et al. |
| 4,235,906 A | | 11/1980 | Savarese et al. |
| 4,491,665 A | | 1/1985 | El-Sayad et al. |
| 4,556,712 A | | 12/1985 | Rice |
| 4,666,918 A | | 5/1987 | Ivanova et al. |
| 4,686,228 A | | 8/1987 | Campbell et al. |
| 4,701,460 A | | 10/1987 | El-Sayad et al. |
| 4,707,485 A | | 11/1987 | Kaiser et al. |
| 4,727,146 A | | 2/1988 | Rice |
| 4,727,147 A | | 2/1988 | Wintermeyer et al. |
| 4,761,418 A | | 8/1988 | Swaringen, Jr. et al. |
| 5,240,939 A | | 8/1993 | Demko |
| 5,438,140 A | | 8/1995 | Oftring et al. |
| 5,453,510 A | | 9/1995 | Hill et al. |
| 5,556,978 A | | 9/1996 | Hill et al. |
| 5,684,154 A | | 11/1997 | Chamberlin et al. |
| 6,177,445 B1 | | 1/2001 | Bigham et al. |
| 6,187,789 B1 | | 2/2001 | Bigham et al. |
| 6,194,421 B1 | | 2/2001 | Cohen et al. |
| 6,548,521 B1 | | 4/2003 | Cohen et al. |
| 6,562,836 B1 | | 5/2003 | Szarek et al. |
| 6,858,750 B2 | | 2/2005 | Joshi |
| 7,037,489 B2 | | 5/2006 | Uchiwa et al. |
| 2003/0149082 A1 | | 8/2003 | Makriyaannis et al. |
| 2003/0191115 A1 | | 10/2003 | Pinto et al. |
| 2004/0054001 A1 | | 3/2004 | Joshi et al. |
| 2004/0180925 A1 | | 9/2004 | Matsuno et al. |
| 2005/0192243 A1 | | 9/2005 | Savarese |
| 2006/0177408 A1 | | 8/2006 | Uchiwa et al. |
| 2006/0205659 A1 | | 9/2006 | Joshi et al. |

FOREIGN PATENT DOCUMENTS

| | | | | |
|---|---|---|---|---|
| EP | 0008824 A1 | | 3/1980 |
| EP | 1380573 A2 | | 1/2004 |
| EP | 1526130 A1 | | 4/2005 |
| EP | 1676580 | * | 7/2006 |
| WO | WO-98/42674 A1 | | 10/1998 |
| WO | WO-98/42675 A1 | | 10/1998 |
| WO | WO-9842675 A1 | * | 10/1998 |
| WO | WO-9847534 A1 | * | 10/1998 |
| WO | WO-2005/041960 A2 | | 5/2005 |
| WO | WO-2007074454 A2 | * | 7/2007 |
| WO | WO-2008/070121 A1 | | 6/2008 |
| WO | WO-2010107488 A1 | * | 9/2010 |
| WO | WO-2011022491 A1 | * | 2/2011 |

OTHER PUBLICATIONS

"U.S. Appl. No. 10/975,197, Advisory Action mailed Jan. 24, 2007", 3 pgs.
"U.S. Appl. No. 10/975,197, Amendment and Response filed Oct. 30, 2007 to Final Office Action mailed Oct. 18, 2007", 17 pgs.
"U.S. Appl. No. 10/975,197, Amendment and Response filed Dec. 22, 2006 to Final Office Action mailed Sep. 26, 2006", 13 pgs.
"U.S. Appl. No. 10/975,197, Amendment and Response filed Jul. 30, 2007 to Non-Final Office Action mailed May 2, 2007", 17 pgs.
"U.S. Appl. No. 10/975,197, Declaration, Amendment and Response filed Jul. 24, 2006 to Non-Final Office Action mailed Feb. 24, 2006", 23 pgs.
"U.S. Appl. No. 10/975,197, Final Office Action mailed Sep. 26, 2006", 16 pgs.
"U.S. Appl. No. 10/975,197, Non-Final Office Action mailed Feb. 24, 2006", 9 pgs.
"U.S. Appl. No. 10/975,197, Non-Final Office Action mailed May 2, 2007", 13 pgs.
"U.S. Appl. No. 10/975,197, Response filed Jan. 13, 2006 to Restriction Requirement mailed Dec. 27, 2005", 10 pgs.
"U.S. Appl. No. 10/975,197, Restriction Requirement mailed Dec. 27, 2005", 5 pgs.
"U.S. Appl. No. 10/975,197, Final Office Action mailed Oct. 18, 2007", 15 pgs.
"U.S. Appl. No. 10/975,197, Non-Final Office Action mailed Feb. 4, 2008", 17 pgs.
"Le Chatelier's Principle", [online]. © Jim Clark 2002. Retrieved from the Internet: <URL: http://www.chemguide.co.uk/physical/equilibria/lechatelier.html>, (2002), 6 pgs. "PCT Application No. PCT/US07/24914, International Search Report mailed Apr. 17, 2008", 3 pgs.
"PCT Application No. PCT/US07/24914, Written Opinion mailed Apr. 17, 2008", 8 pgs.
"PCT Application No. PCT/US2004/035869, International Search Report mailed May 3, 2005", 3 pgs.
"PCT Application No. PCT/US2004/035869, International Preliminary Report on Patentability and Written Opinion mailed May 11, 2006", 9 pgs.
"Rate equation", Retrieved from the Internet: <URL: http://en.wikipedia.org/wiki/rRate_equation>, The Free Encyclopedia, (2006), 6 pgs.

(Continued)

*Primary Examiner* — Zinna Northington Davis
(74) *Attorney, Agent, or Firm* — Schwegman, Lundberg & Woessner P.A.

(57) ABSTRACT

The invention provides novel neuromuscular blocking agents, methods of using the neuromuscular blocking agents as well as reagents, methods and kits for reversing the effects of the neuromuscular blocking agents.

22 Claims, 11 Drawing Sheets

OTHER PUBLICATIONS

Agoston, S., et al., "The Neuromuscular Blocking Action of Org NC 45, A New Pancuronium Derivative, in Anaesthetized Patients", *British Journal of Anaesthesia*, 52(Supplement 1), (1980), 53S-59S.
Baird, W. L., et al., "A New Neuromuscular Blocking Drug, Org NC 45", *British Journal of Anaesthesia*, 52(Supplement 1), (1980), 61S-62S.
Bedford, R. F., "From the FDA", *Anesthesiology*, 82, (1995), p. 33A.
Belmont, M. R., "Succinylcholine/Suxamethonium", *Current Opinion in Anaesthesiology*, 8, (1995), 362-366.
Bencini, A. , et al., "Use of the Human "Isolated Arm" Preparation to Indicate Qualitative Aspects of a New Neuromuscular Blocking Agent, Org NC 45", *British Journal of Anaesthesia*, 52(Supplement 1), (1980), 43S-47S.
Bevan, D. R., "Newer Neuromuscular Blocking Agents", *Pharmacology & Toxicology*, 74(1), (1994), 3-9.
Boros, E. E., "Neuromuscular Blocking Activity and Therapeutic Potential of Mixed-Tetrahydroisoquinolinium Halofumarates and Halosuccinates in Rhesus Monkeys", *Journal of Medicinal Chemistry*, 46, (2003), 2502-2515.
Buckett, W. R., et al., "Pancuronium Bromide and Other Steroidal Neuromuscular Blocking Agents Containing Acetylcholine Fragments", *Journal of Medicinal Chemistry*, 16(10), (1973), 1116-1124.
Buzello, W., "The New Non-Depolarizing Muscle Relaxant Org NC 45 in Clinical Anaesthesia: Preliminary Results", *British Journal of Anaesthesia*, 52(Supplement 1), (1980), 62S-64S.
Crul, J. F., et al., "First Clinical Experiences With Org NC 45", *British Journal of Anaesthesia*, 52(Supplement 1), (1980),49S-52S.
De Rosa, S. C., "N-acetylcysteine Replenishes Glutathione in HIV Infection", *European Journal of Clinical Investigation*, 30, (2000),915-929.
Dizdar, N., et al., "Comparison of *N*-acetylcysteine and L-2-oxothiazolidine-4-Carboxylate as Cysteine Deliverers and Glutathione Precursors in Human Malignant Melanoma Transplants in Mice", *Cancer Chemother Pharmacol*, 45, (2000), 192-198.
Durant, N. N., et al., "Suxamethonium", *British Journal of Anaesthology*, 54, (1982), 195-208.
Fahey, M. R., et al., "Clinical Pharmacology of ORG NC45 (Norcuron™): A New Nondepolarizing Muscle Relaxant", *Anesthesiology*, 55(1), (1981),6-11.
Foldes, F. F., et al., "Influence of Halothane and Enflurane on the Neuromuscular Effects of Org NC 45 in Man", *British Journal of Anaesthesia*, 52(Supplement 1), (1980), 64S-65S.
Huang, T. C., et al., "Mechanistic Studies on Thiazolidine Formation in Aldehyde/Cysteamine Model Systems", *J Agric Food Chem.*, 46(1), (1998), 224-227.
Kharkevich, D. A., "New Curare-Like Agents", *J. Pharm. Pharmac.*, 26, (1974), 153-165.
Khromov-Borisov, N. V., et al., "Removal of a Curare-Like Effect by Direct Inactivation of the Myorelaxant Molecule by Disruption of the Disulfide Bond", *Doklady Biological Sciences, Proceedings of the Academy of Sciences of the USSR*, 186(1), (1968), 460-463.
Kreig, N., et al., "Preliminary Review of the Interactions of Org NC 45 With Anaesthetics and Antibiotics in Animals", *British Journal of Anaesthesia*, 52(Supplement 1), (1980), 33S-36S.
Lee, C., "Structure, Conformation, and Action of Neuromuscular Blocking Drugs", *British Journal of Anaesthesia* , 87(5), (2001), 755-769.
Li, J. , et al., "Dietary Supplements With Cysteine Produgs Selectively Restores Tissue Glutathione Levels and Redox Status in Protein-Malnourished Mice", *Journal of Nutritional Biochemistry*,13, (2002), 625-633.
Lien, C. A., "The Pharmacology of GW280430A: A New Nondepolarizing Neuromuscular Blocking Agent", *Seminars in Anesthesia: Perioperative Medicine and Pain*, 21 (2), (2002), 86-91.
Mahajan, R. P., "Focus on: Controversies in Anaesthesia—Is Suxamethonium Now Obsolete?", *Cuurent Anaesthesia and Critical Care*, 7, (1996), 289-294.
Marshall, R. J., et al., "Comparison of the Cardiovascular Actions of Org NC 45 With Those Produced by Other Non-Depolarizing Neuromuscular Blocking Agents in Experimental Animals", *British Journal of Anaesthesia*, 52(Supplement 1), (1980),21S-32S.
Marshall, I. G., et al., "Pharmacology of Org NC 45 Compared With Other Non-Depolarizing Neuromuscular Blocking Drugs", *British Journal of Anaesthesia*, 52(Supplement 1), (1980),11S-19S.
McNulty, M., "The Ultra-Short Acting Nondepolarizing Relaxant GW280430A Undergoes Rapid Degradation by Chemical Mechanisms", (Abstract Only), *Anesthesiology Abstracts of Scientific Papers Annual Meeting—2002*, 1 pg.
Miller, R. D., "Org NC 45", *British Journal of Anaesthesia*, 52(Supplement 1), (1980), 71S-72S.
Naguib, M. , et al., "Advances in Neurobiology of the Neuromuscular Junction", *Anesthesiology*, 96(1), (2002),202-231.
Norman, J., et al., "Introduction", *British Journal of Anaesthesia*, 52(Supplement 1), (1980), S1-S2.
Rees, D. C., et al., "Chapter 5. Drugs in Anesthetic Practice", *Annual Reports in Medicinal Chemistry*, 31, (1994), 41-50.
Reese, M. J., "Comparative Metabolic Profiles of the Neuromuscular Blocker GW280430 in Human, Monkey, and Dog, and Characterization of a Major Metabolite as an Unusal Cyclized Cysteine Conjugate", *Presented at the 9th North American ISSX Meeting* (*issx.org*); Nashville, TN, (Abstract No. 282),(Oct. 1999), p. 142.
Saitoh, Y., et al., "Infusion of Amino Acid Enriched Solution Hastens Recovery From Neuromuscular Block Caused by Vecuronium", *British Journal of Anaesthesia*, 86, (2001), 814-821.
Sakuraba, H., et al., "Asymmetric Michael Addition of Aromatic Thiols to 2-Cyclohexenone and Maleic Acid Esters Via Formation of Crystalline Cyclodextrin Complexes", *Journal of Inclusion Phenomena and Molecular Recognition in Chemistry*, (1991),195-204.
Savage, D. S., et al., "The Emergence of ORG NC 45, 1-[(2β,3α,5α,16β,17β)-3, 17-Bis(Acetyloxy)-2-(1-Piperidinyl)-Androstan-16-YL]-1-Methylpiperidinium Bromide, From the Pancuronium Series", *British Journal of Anaesthesia*, 52(Supplement 1), (1980), 3S-9S.
Savarese, J. J., et al., "Chapter 14. Pharmacology of Muscle Relaxants and Their Antagonists", *In: Anesthesia*, vol. 1, (Fourth Edition), Miller, R. D., et al., Editors, Churchill Livingstone Inc.,(1999),417-487.
Schaer, H., et al., "Preliminary Clinical Observations With Org NC 45", *British Journal of Anaesthesia*, 52(Supplement 1), (1980),65S-67S.
Son, S. L., et al., "A Comparison of the Neuromuscular Blocking and Vagolytic Effects of ORG NC45 and Pancuronium", *Anesthesiology*, 55(1), (1981),12-18.
Speight, T. M., et al., "Pancuronium Bromide: A Review of its Pharmacological Properties and Clinical Application", *Drugs*, 4(1-2), (1972), 163-226.
Van Der Veen, F., et al., "Pharmacokinetics and Pharmacodynamics of Org NC 45 in Man", *British Journal of Anaesthesia*, 52(Supplement 1), (1980), 37S-41S.
Viby-Mogensen, J., et al., "On Org NC 45 and Halothane Anaesthesia", *British Journal of Anaesthesia*, 52(Supplement 1), (1980), 67S-69S.
Zhang, L., et al., "Thiazolidine Formation as a General and Site-Specific Conjugation Method for Synthetic Peptides and Proteins", *Anal Biochem.*, 233(1), (1996), 87-93.
"Chinese Application Serial No. 200780050532.4, Office Action mailed Sep. 20, 2010", (w/ English Translation), 10 pgs.
"European Application Serial No. 07862551.4, Extended European Search Report mailed Oct. 29, 2010", 7 pgs.
"Japanese Application Serial No. 2009-540280, Amendment and Request for Examination filed Dec. 3, 2010", 92 pgs.
Boros, E. E, et al., "Bis- and mixed-tetrahydroisoquinolinium chlorofumarates: New ultra-short-acting nondepolarizing neuromuscular blockers", *Journal of Medicinal Chemistry*, 42(2), (1999), 206-209.
Morrison, R. T., et al., *In: Organic Chemistry* (*Second Edition*), Allyn and Bacon, Inc., Boston, MA, (1966), 290-293.
Nebergall, W. H., "Chapter 7—Molecular Structure and Hybridization", *In: General Chemistry* (*6th Edition*), D. C. Heath and Company, (1980), 149-152.
"Chinese Application Serial No. 200780050532.4, Office Action response filed Feb. 5, 2011 to Office Action mailed Sep. 20, 2010", 16 pgs.
"Canadian Application Serial No. 2,671,904, Response filed Sep. 14, 2011 to Office Action mailed Jun. 23, 2011", 30 pgs.

"European Application Serial No. 07862551.4, Extended European Search Report response filed Jun. 2, 2011", 9 pgs.
Savarese, J. J, et al., "Rapid chemical antagonism of neuromuscular blockade by L-cysteine adduction to and inactivation of the olefinic (double-bonded) isoquinolinium diester compounds gantacurium (AV430A), CW 002, and CW 011.", Anesthesiology, 113(1), (Jul. 2010), 58-73.
Sunaga, H., et al., "Cysteine reversal of the novel neuromuscular blocking drug CW002 in dogs: pharmacodynamics, acute cardiovascular effects, and preliminary toxicology.", Anesthesiology, 112(4), (Apr. 2010), 900-9.
"Database WPI Week 199309", Thomson Scientific, London, GB; AN 1993-071085, XP002605917, JP 5 017431 A (Seiko Epson Corp), (Jan. 26, 1993).*
"Database WPI Week 200923", Thomson Scientific, London, GB; AN 2009-G02209 XP002605916, CN 101' 366 695 A (Jiangsu Sihuan Biological Co Ltd), (Feb. 18, 2009).*
"International Application Serial No. PCT/US 2010/000796, Search Report mailed Aug. 4, 2010", 2 pgs.*
"International Application Serial No. PCT/US10/45907, Written Opinion mailed Nov. 10, 2010", 7 pgs.*
"International Application Serial No. PCT/US2010/000796, Written Opinion mailed Aug. 4, 2010", 13 pgs.*
"International Application Serial No. PCT/US2010/45907 , Written Opinion Mailed Nov. 10, 2010", 8 pgs.*
Kulawska, et al., "Kinetics of the esterification of maleic anhydride with octyl", decyl or dodecyl 68-69 alcohol over dowex catalyst. Reaction Kinetics and Catalysis Letters, vol. 85 (1), Abstract only, (2005), pp. 51-56.*

* cited by examiner

INTERMEDIATE DURATION NEUROMUSCULAR BLOCKING AGENTS AND ANTAGONISTS THEREOF

CONTINUING DATA

This application claims the benefit of U.S. Provisional Ser. No. 60/873,132 filed Dec. 6, 2006, which application is specifically incorporated herein by reference in its entirety.

RELATED APPLICATIONS

This application is also related to U.S. application Ser. No. 10/975,197 filed Oct. 28, 2004, now abandoned; PCT Application Serial No. PCT/US2004/035869 filed Oct. 28, 2004; and U.S. application Ser. No. 60/515,048 filed Oct. 28, 2004, the contents of each of which applications are specifically incorporated herein by reference in their entireties.

FIELD OF THE INVENTION

The invention relates to intermediate acting neuromuscular blocking agents and methods for using and counteracting the effects of such neuromuscular blocking agents.

BACKGROUND OF THE INVENTION

Administration of the long-acting neuromuscular blocker (NMB) d-tubocurarine (curare) (1a) to induce skeletal muscle relaxation during surgery and facilitate tracheal intubation maneuvers transformed the practice of anesthesia. Savarese et al., Pharmacology of Muscle Relaxants and Their Antagonists. In *Anesthesia,* 4th ed.; Miller, R. D., Ed.; Churchill Livingstone: New York, 1994; pp 417-488. Since that time a variety of semi-synthetic and synthetic neuromuscular blockers with varying durations of NMB (curare-like) activity became available in the clinic. Id.; Lee, *Br. J. Anaesth.* 2001, 87, 755-769; Rees et al., *Annu. Rep. Med. Chem.* 1996, 31, 41-50; Bevan, *Pharmacol. Toxicol.* 1994, 74, 3-9.

Neuromuscular blockers are categorized both by their mechanism of action (nondepolarizing or depolarizing) and by their duration of action (ultra-short, short-, intermediate-, and long-acting). The maximum clinical duration of such neuromuscular blocker as defined by the FDA is the time for return to 25% of control in a twitch response test after a dose of twice the 95% effective dose ($ED_{95}$). This maximum duration time for an ultra-short neuromuscular blocker is 8 minutes, for a short neuromuscular blocker the duration is 20 minutes, for an intermediate neuromuscular blocker the duration time is 50 minutes and the duration time for a long acting neuromuscular blocker is greater than 50 minutes. See Bedford, *Anesthesiology* 1995, 82, 33A.

Examples of these neuromuscular blocking adjuncts to anesthesia include the long-acting agent metocurine (1b), the ultra-short-acting succinylcholine (2), the short-acting relaxant mivacurium (3), and the long-acting agent doxacurium (4).

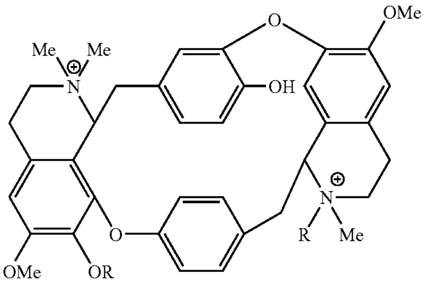

1a: R = H (d-tubocurarine)
1b: R = Me (metocurine)

-continued

2

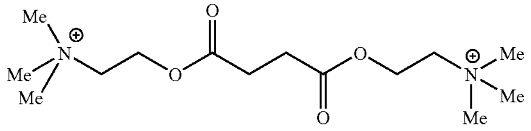

(succinylcholine)

3

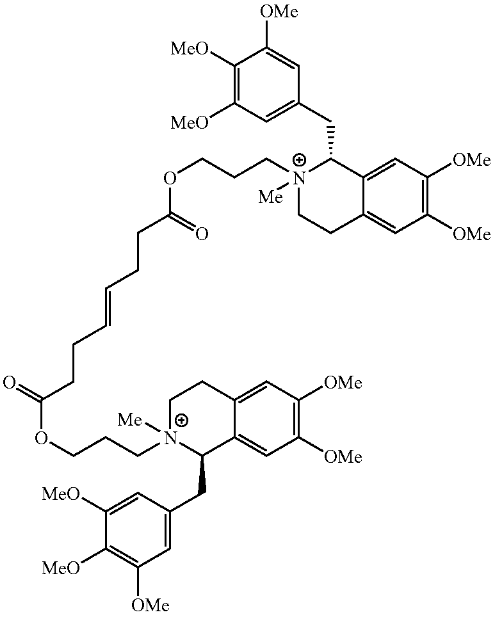

(mivacurium)

4

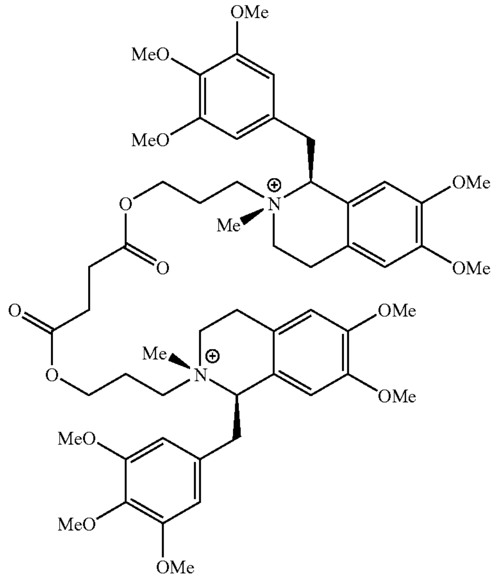

(doxacurium = meso + dl-forms)

The benzyltetrahydroisoquinoline-based, therefore relaxants are nondepolarizing neuromuscular blockers.

Succinylcholine (2) is a depolarizing agent. Depolarizing neuromuscular blockers are nicotinic acetylcholine receptor agonists and produce a number of unwanted side-effects associated with their mechanism of action. Naguib et al., *Anesthesiology* 2002, 96, 202-231; Mahajan, *Curr. Anaesth. Crit.*

*Care* 1996, 7, 289-294; Belmont, *Curr. Opin. Anesthesiol.* 1995, 8, 362-366; Durant et al., *Br. J. Anaesth.* 1982, 54, 195-208. These untoward effects can, in rare instances, include anaphylaxis, hyperkalemia, malignant hyperthermia, and cardiac arrhythmias. More common side-effects of depolarizing neuromuscular blockers include fasciculations, severe muscle pain, increased intraocular pressure, and increased intragastric tension.

Although a variety of long-, intermediate-, and short-acting neuromuscular blockers exist in the clinic, methods for reversing the effects of these neuromuscular blocking agents are slow and give rise to undesirable side effects, some of which can be life-threatening. Hence, new intermediate neuromuscular blockers and new methods for controlling the duration of intermediate neuromuscular blockade are needed.

SUMMARY OF THE INVENTION

The invention relates to novel intermediate neuromuscular blocking agents. Other aspects of the invention include methods, compositions and kits for controlling the maximum clinical duration of these intermediate neuromuscular blocking agents. In one embodiment, the methods of the invention involve fast-acting agents that antagonize the neuromuscular blockade caused by administration of the present intermediate neuromuscular blocking agents. Agents that can antagonize the neuromuscular blockade caused by administration of the present neuromuscular blocking agents include cysteine, N-acetylcysteine, glutathione, as well as related cysteine analogs and combinations thereof.

Hence, one aspect of the invention is a neuromuscular blocking agent selected from the group consisting of:

AV001

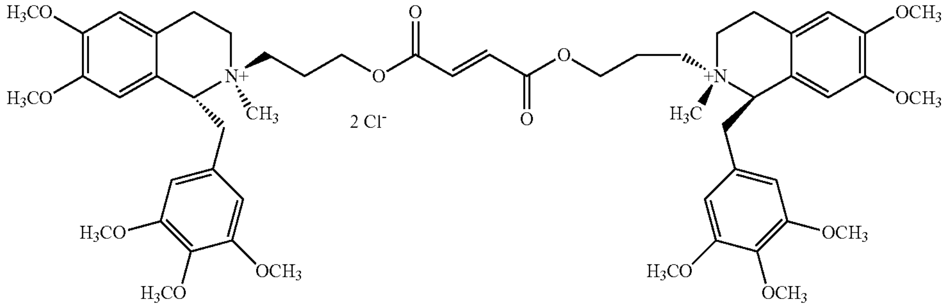

AV002

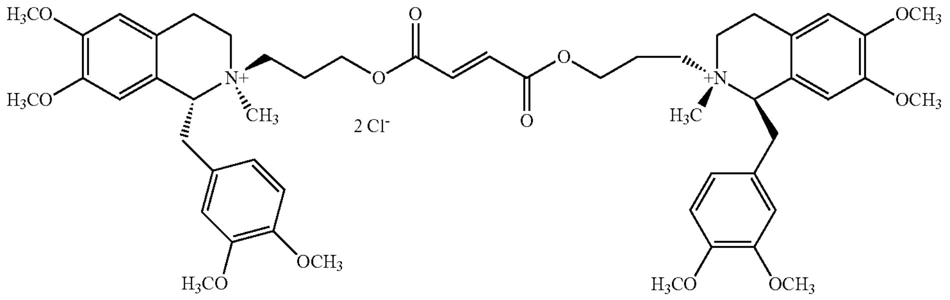

AV003

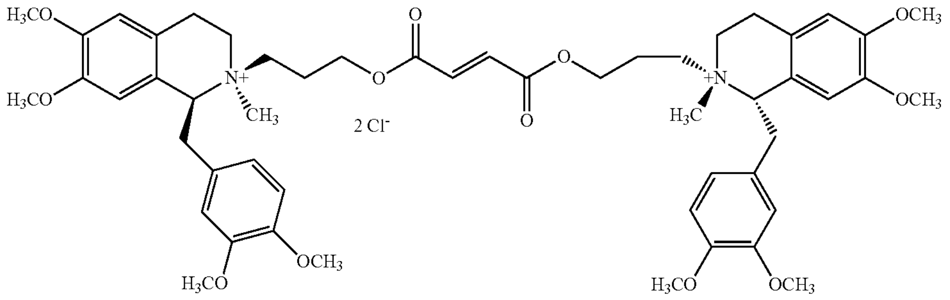

AV005

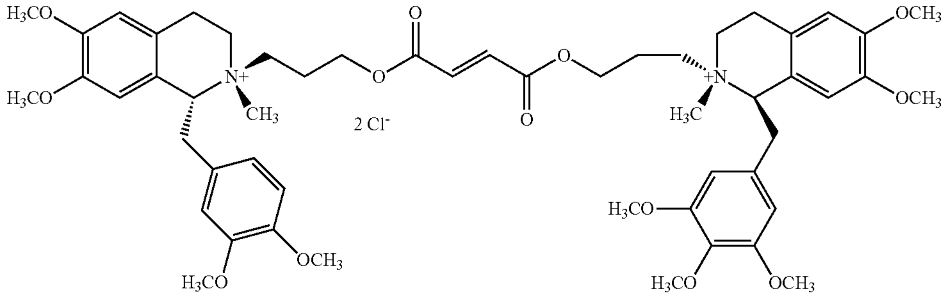

-continued

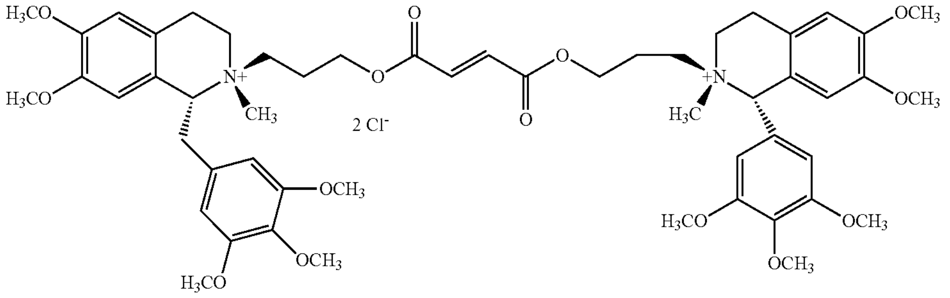

AV006

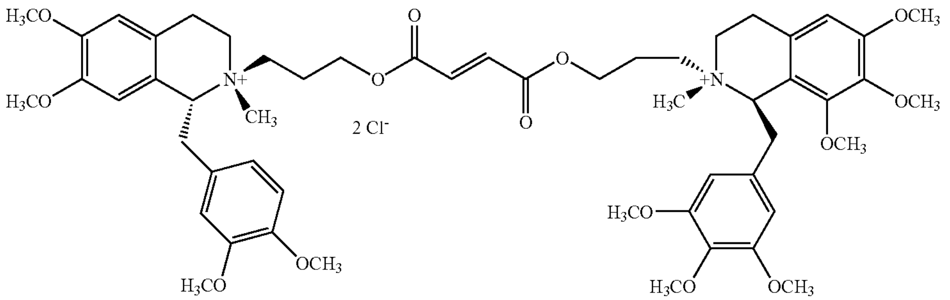

AV007

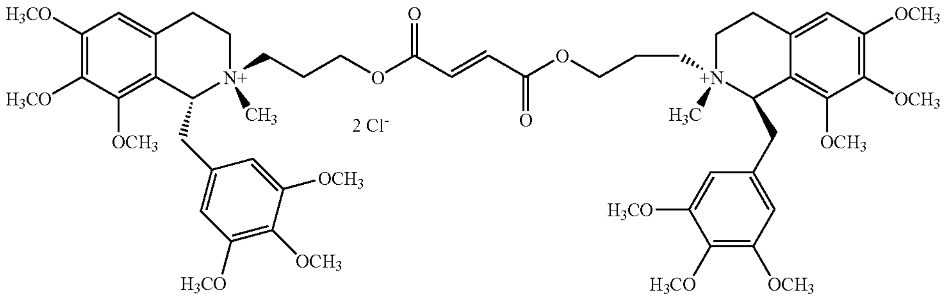

AV008 and combinations thereof.

Another aspect of the invention is a therapeutic method of generating a neuromuscular blockade in a mammal comprising administering to the mammal an effective amount of a neuromuscular blocking agent of the invention.

Another aspect of the invention is a therapeutic method of antagonizing a neuromuscular blockade caused by administration to a mammal of a neuromuscular blocking agent of the invention, wherein the method comprises administering an effective amount of a neuromuscular blockade antagonist to the mammal. Examples of neuromuscular blockade antagonists include cysteine, glutathione, N-acetylcysteine, homocysteine, methionine, S-adenosyl-methionine, penicillamine, a related cysteine analog, a combination thereof or a pharmaceutically acceptable salt thereof. In some embodiments, the antagonist is cysteine. In other embodiments, the antagonist is cysteine combined with glutathione. In other embodiments, the antagonist is cysteine or glutathione combined with any of the other antagonists. For example, in some embodiments, the combination of cysteine and glutathione is particularly effective.

The invention further provides a kit that includes, separately packaged, (a) at least one of the present neuromuscular blocking agents in an amount sufficient to relax or block skeletal muscle activity, and (b) an amount of an antagonist to the neuromuscular blocking agent(s) effective to reverse the effects of the blocking agent on a mammal, with (c) instructions explaining how to administer the neuromuscular blocking agent to a mammal and how to employ the antagonist to reverse the effects of the blocking agent on the mammal to which the blocking agent was administered. Such an antagonist to a neuromuscular blocking agent can, for example, be cysteine, glutathione, N-acetylcysteine, homocysteine, methionine, S-adenosyl-methionine, penicillamine, a combination thereof or pharmaceutically acceptable salts thereof in combination. In some embodiments, the antagonist is cysteine. In other embodiments, the antagonist is cysteine combined with a cysteine analog. For example, in some embodiments, the combination of cysteine and glutathione is particularly effective.

DETAILED DESCRIPTION OF THE INVENTION

Figure 1:
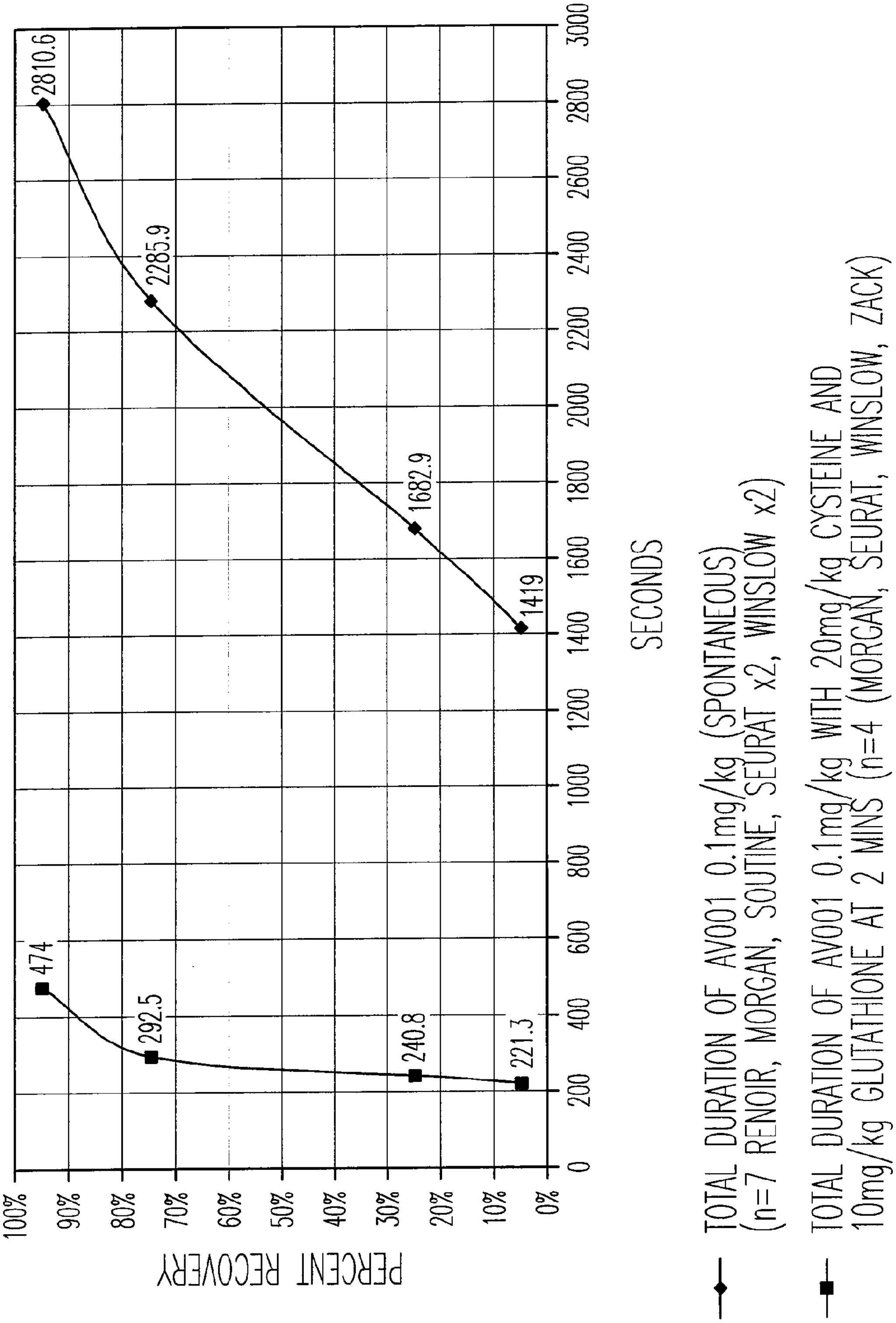
FIG. 1 graphically illustrates the duration of neuromuscular blockade in monkeys caused by administration of 0.1 mg/kg AV001 neuromuscular blocking agent with (■) and without (♦) administration of neuromuscular blockade antagonists (a combination of 20 mg/kg cysteine and 10 mg/kg glutathione). As indicated spontaneous recovery from administration of AV001 takes about 2800 seconds (about 46 min.). However, when a combination of cysteine and glutathione is administered at 2 minutes post-administration of AV001, recovery from the neuromuscular blockade takes only about 354 seconds (about 6 min.).

The present invention relates to novel neuromuscular blocking agents of intermediate duration and methods for regulating the duration of these neuromuscular blocking agents.

Neuromuscular blocking agents can literally paralyze a patient for the time during which they are active. Hence, the use of neuromuscular blocking agents is restricted to situations where muscle relaxation is essential for effective treatment of a patient, for example, selected surgical procedures and those involving intubation of the trachea. Because paralysis can interfere with essential body functions (e.g. breathing) the physician selects a neuromuscular blocking agent that will be active for as long as needed but no more than is needed. For example, when a breathing tube must be inserted into the trachea of a patient a neuromuscular blocking agent is used to relax the tracheal muscles and permit intubation. However, the neuromuscular blocking agent also relaxes the muscles of the chest, thereby causing the patient to stop breathing. The anesthesiologist must quickly insert the breathing tube into the patient's trachea and begin ventilation of the lungs. If the tube cannot be inserted quickly enough, the physician must intervene with some form of artificial resuscitation or the patient may suffer oxygen deprivation, and the associated tissue damage from lack of oxygen. Fast reversal of the neuromuscular blocking agent by a rapidly acting antagonist can remove the patient from danger and avoid sustained artificial resuscitation.

In addition to providing new intermediate duration neuromuscular blocking agents, the invention provides methods of using these blocking agents and fast, reliable methods for counteracting the effects of these intermediate duration neuromuscular blocking agents so that a patient will recover from the effects of such neuromuscular blocking agents within a few minutes after administering the appropriate antagonist.

The compounds of the invention are safer and more reliable neuromuscular blocking agents than currently available combinations of neuromuscular agents and antagonists, particularly because the neuromuscular blockade can be counteracted with cysteine and cysteine-like molecules at any time, even just after administration of the blocking agent. This cannot be done with currently available neuromuscular blocking agents and antagonists. Currently, an anesthesiologist must wait until a patient is spontaneously beginning to recover from currently available neuromuscular blocking agents before administering antagonists that are commonly available at this time. In the case of currently available neuromuscular blocking agents this waiting time may from 30 to 60 minutes or more.

In contrast, the reversal agents of the invention effectively remove the neuromuscular blockade caused by the present blocking agents within a few minutes. The cysteine and cysteine-like antagonists of the invention also have substantially no side effects. The antagonists of the invention are compounds that are naturally found in the body and cause essentially no change in pulse rate, blood pressure or other indicators of cardiac function. The cysteine and cysteine-like antagonists of the invention act directly on neuromuscular blocking agents and quickly convert them to inactive chemical derivatives. The cysteine and cysteine-like antagonists of the invention do not require inhibition of an important endogenous enzyme system, which is required by currently available antagonists of neuromuscular blocking agents such as neostignine, edrophonium and other cholinesterase inhibitors.

Neuromuscular Blocking Agents

The neuromuscular blocking agents of the invention have the following structures.

AV001

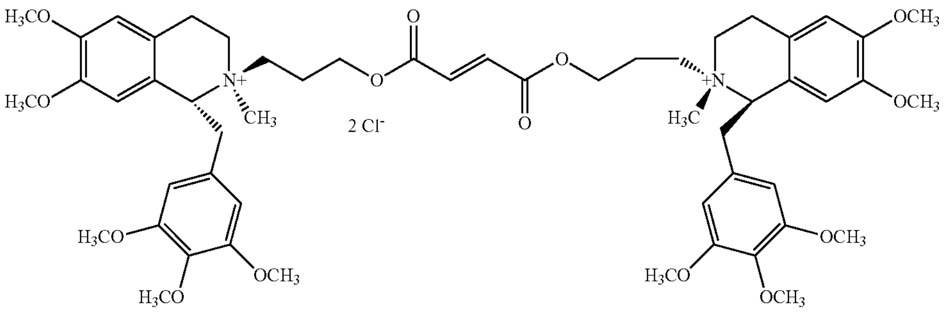

AV002

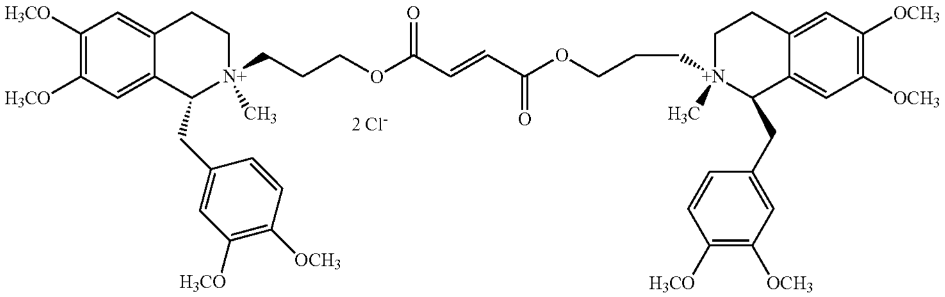

AV003

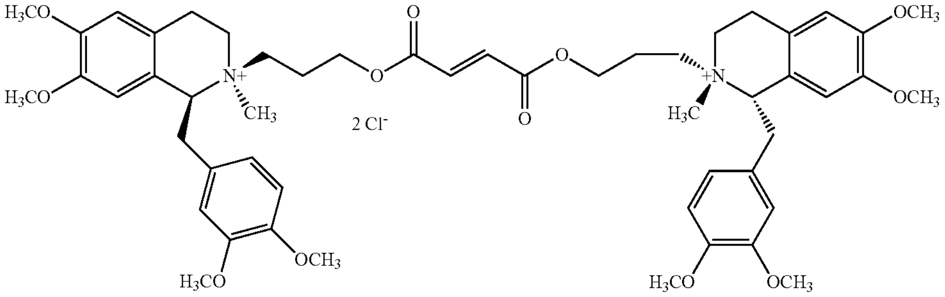

AV005

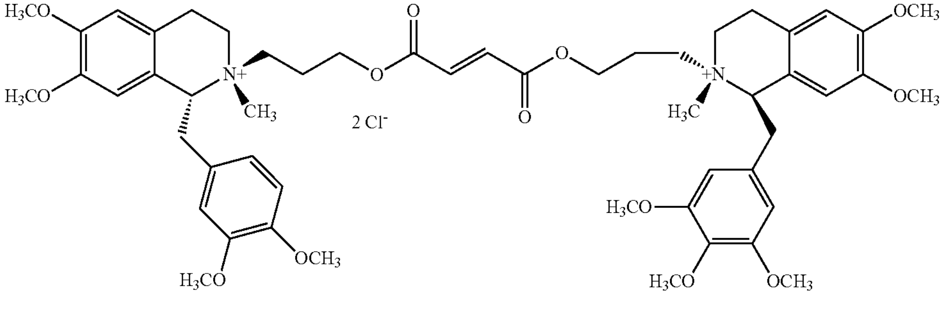

-continued

AV006

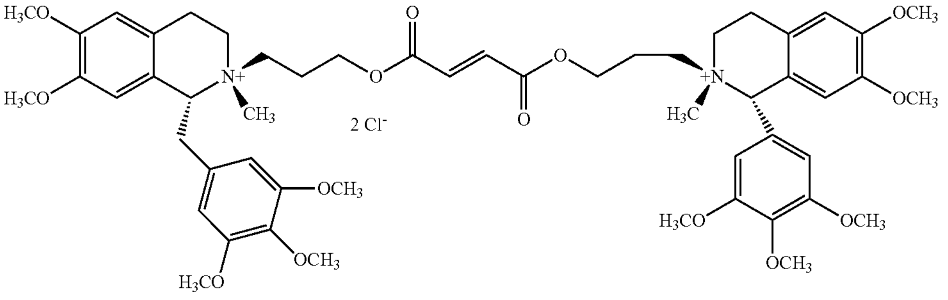

AV007

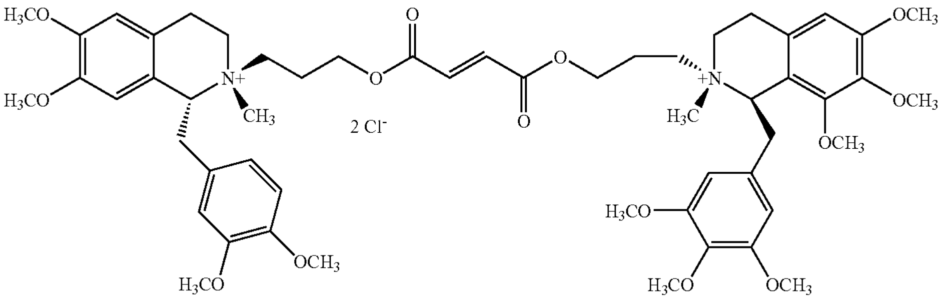

AV008

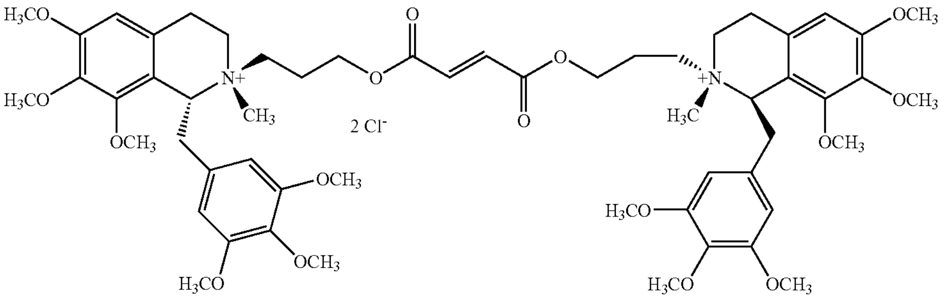

and combinations thereof.

Neuromuscular Blockade Antagonists

According to the invention, cysteine, N-acetylcysteine, glutathione, related cysteine analogs and combinations thereof can be used to shorten the duration of the present neuromuscular blocking agents. While the inventor has previously observed that cysteine can reverse the neuromuscular blockade of chlorofumarate neuromuscular blocking agents, the chlorine on these blocking agents was thought to be needed for cysteine reversal. However the present neuromuscular blocking agents have no chlorine or other halide. Thus, it is surprising that cysteine, glutathione and other cysteine-like antagonists can rapidly and fully reverse the neuromuscular blockade caused by administration of the present agents.

Note that cysteine-like molecules such as cysteine and glutathione have no reversal effect whatsoever on recovery from blockades produced by other benzylisoquinolinium-based neuromuscular blocking drugs such as mivacurium, doxacurium and cisatracurium. Therefore, as illustrated herein, reversal by cysteine-like antagonists is effective when the neuromuscular blocking agent has a fumarate double bond, where activating carboxyl groups are immediately adjacent (i.e., α-) to the double bond. Note further that, although mivacurium contains a double bond in the center of the molecule, this bond is separated from the carboxyl groups by two carbon atoms. Thus, a neuromuscular blockade caused by mivacurium cannot be reversed by a cysteine-like molecule. In addition, the inventors have found that while blockades caused by chlorofumarates can be reversed by cysteine, other halogenated agents, for example, like those listed by Bigham et al. (U.S. Pat. No. 6,177,445), including fluorofumarates and difluorosuccinates, are unaffected by cysteine/glutathione.

Moreover, the compounds listed by Bigham et al. are described as ultra-short acting and are all halogenated. The compounds of the present invention are particularly unique in that they are not halogenated, are intermediate in duration, and can be rapidly reversed by cysteine/glutathione because of the presence of the fumarate double bond and the activating adjacent carboxyl groups. It is believed that the compounds of the present invention are the only non-chlorinated neuromuscular blocking agents whose effects can be rapidly terminated, at any time, by one of the present antagonists, or a combination thereof.

The antagonist molecules used in the methods of the invention include any substantially nontoxic compound having a sulfhydryl and/or amino substituent that can reduce the duration of a neuromuscular blockade caused by one of the present neuromuscular blocking agents. Examples of such antagonists include cysteine, N-acetylcysteine, glutathione, homocysteine, methionine, S-adenosyl-methionine, penicillamine and related cysteine analogs.

Methods of Use

One aspect of the invention is a method of inducing paralysis or a neuromuscular blockade in a mammal by administering an effective amount of one of the present neuromuscular blocking agents.

The present invention also provides a method for reversing the paralysis or the neuromuscular blockade in a mammal that caused by the present neuromuscular blocking agents, by administering to the mammal an amount of a cysteine or cysteine-like molecule that is effective for reversing the neuromuscular block produced by a neuromuscular blocking agent of the invention.

The effective amount or dosage of the present neuromuscular blocking agents for each subject may vary. However, an effective amount or dosage of the present neuromuscular blocking agent to obtain paralysis in mammals is about 0.01 to 20.0 mg/kg of body weight, or about 0.02 to 2.0 mg/kg of body weight, where this dosage is based on the weight of the di-cation, which is the active ingredient. If intramuscular administration is preferred, the dosage is about two to eight times that employed for an intravenous dose. Thus, the intramuscular dosage is about 0.02 to 80.0 mg/kg of body weight, or about 0.04 to 8.0 mg/kg of body weight.

Another aspect of the present invention is a kit containing one or more of the present neuromuscular blocking agents with an effective amount of cysteine or a cysteine-like molecule for use in therapy, for example to induce neuromuscular blockade in surgery or for intubation of the trachea, and then to reverse the neuromuscular blockade. The present invention also provides the use of cysteine or a cysteine-like molecule with or without a compound of the invention in the manufacture of a medicament for reversing neuromuscular blockade in a mammal, including in a human.

While it is possible for the cysteine, cysteine-like molecules and/or compounds of the invention to be administered as the bulk active chemicals, it is preferred to present them in the form of a pharmaceutical formulation for parenteral administration. Accordingly, the present invention provides one pharmaceutical formulation which comprises a therapeutically effective amount of a neuromuscular blocking agent of the invention. Moreover, the invention separately provides a therapeutically effective amount of cysteine or cysteine-like molecule, or a combination of cysteine-like molecules, as hereinbefore defined, and a pharmaceutically acceptable carrier.

Where the pharmaceutical formulation is for parenteral administration, the formulation may be an aqueous or non-aqueous solution or mixture of liquids, which may contain bacteriostatic agents, antioxidants, buffers or other pharmaceutically acceptable additives. Alternatively the compounds may be presented as lyophilized solids for reconstitution with water (for injection) or dextrose or saline solutions. Such formulations are normally presented in unit dosage forms such as ampoules or disposable injection devices. They may also be presented in multi-dose forms such as a bottle from which the appropriate dose may be withdrawn. All such formulations should be sterile.

A suitable dose to obtain a neuromuscular blockade for adult humans (150 lbs. or 70 kg) is about 0.1 mg to about 500 mg, or in some embodiments about 1 mg to about 500 mg, or in other embodiments about 0.5 mg to about 150 mg, or in further embodiments about 3.5 mg to about 50 mg. Thus a suitable pharmaceutical parenteral preparation for administration to humans will preferably contain 0.1 to 50 mg/ml of one or more of the present compounds in solution or multiples thereof for multi-dose vials.

A suitable dose of cysteine or a cysteine-like molecule to reverse a neuromuscular blockade in adult humans (with an average weight of about 150 lbs. or 70 kg) is about 5 mg to about 10,000 mg, or about 50 mg to about 2000 mg or about 150 to about 750 mg. Thus a suitable pharmaceutical parenteral preparation for administration to humans will preferably contain 0.1 to 2000 mg/ml of cysteine or a cysteine-like molecule, or a combination of cysteine and cysteine-like molecules, in solution or multiples thereof for multi-dose vials.

Simple formulations of a solution of the present neuromuscular blocking agents, cysteine and/or cysteine-like molecules can be formulated in sterile water or in saline solutions. Of course, the neuromuscular blocking agent and cysteine/cysteine-like agents are prepared as separate solutions or formulations. These solutions may be prepared by dissolving the compound(s) in pyrogen-free water or saline, with or without a preservative and sterilizing the solution. Alternatively, the formulations may be prepared by dissolving the sterile compound in pyrogen-free, sterile water or a sterile physiological saline solution under aseptic conditions. Particularly preferred formulations have a pH of about 2.0 to 5.0.

The neuromuscular blocking agents, cysteine and/or cysteine-like molecules of the invention may also be administered as a rapid intravenous bolus over about 5 seconds to about 15 seconds or, alternatively, as slower infusions over about 1 to about 2 minutes of a saline solution, e.g., Ringer's solution in drip form.

The compounds may also be administered in other solvents (usually as a mixed solvent with water) such as alcohol, polyethylene glycol and dimethylsulphoxide. They may also be administered intravenously or intramuscularly (as a drip if required), either as a suspension or solution.

The following examples further illustrate but are not intended to limit the invention.

EXAMPLE 1

Methods of Administering Neuromuscular Blocking Agents

Rhesus monkeys were anesthetized with ketamine (7.5 mg/Kg) given intramuscularly or intravenously. Anesthesia was maintained with a mixture of isoflurane (1.5%), nitrous oxide (60%) and oxygen (40%). The common peroneal nerve was stimulated supramaximally with square wave pulses of 0.2 m sec duration at a rate of 0.15 Hz. Twitch contractions were recorded via the tendon of the extensor digitorum muscle.

In all animals, the trachea was intubated and ventilation was controlled at 12-15 ml/kg, 18-24 breaths per minute. A peripheral vein and artery were cannulated for drug administration and for recording of arterial pressure, respectively. In preliminary studies a neuromuscular blocking agent having one of the following structures was administered intravenously.

AV001

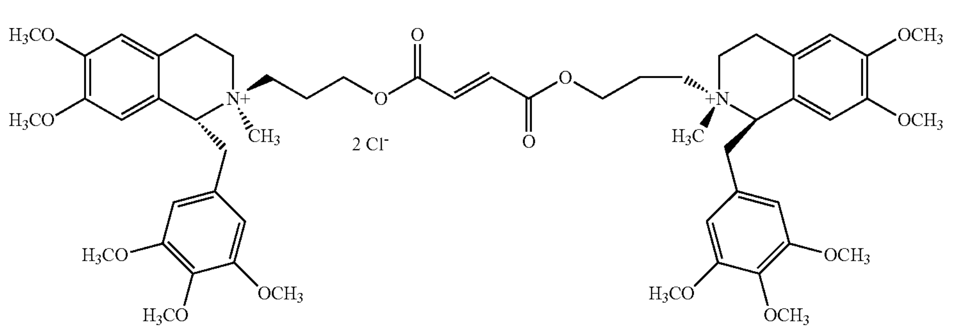

AV002

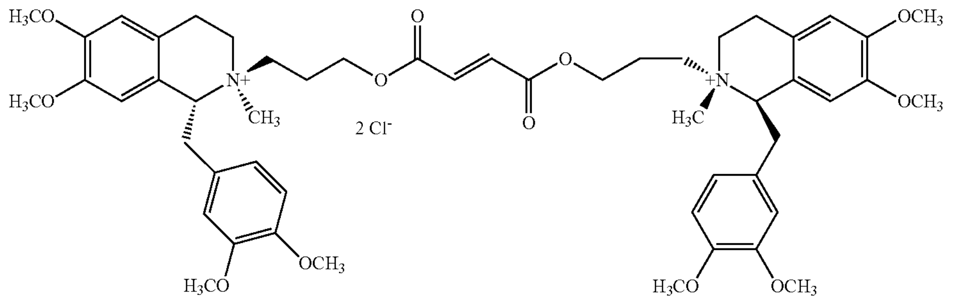

AV003

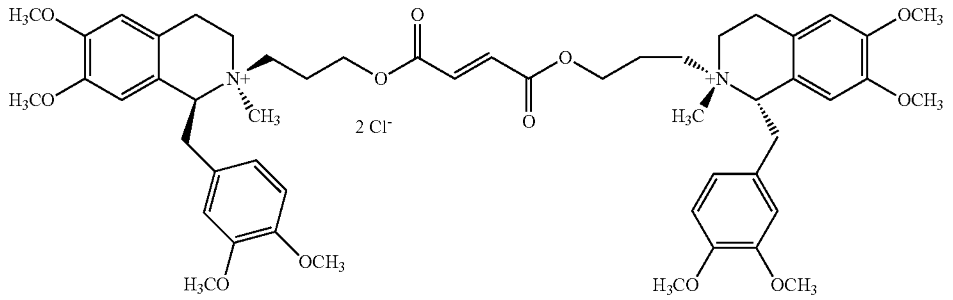

In studies designed to examine the reversal of the neuromuscular blockade caused by these agents, cysteine and/or glutathione was administered to test animals at selected dosages.

EXAMPLE 2

Effective Dosages and Durations of Neuromuscular Agents

Dosage studies indicated that the following dosages were sufficient to achieve neuromuscular blockades for the indicated times.

TABLE 1

Potency and Duration of Blocking Agents*

| Compound | Potency (ED95 mg/kg) | Duration (minutes)** | Duration at 4X ED95 |
|---|---|---|---|
| AV 001 | 0.04 | 30-40 | 50-60 |
| AV 002 | 0.04 | 20-25 | 30-35 |
| AV 003 | 0.20 | 25-40 | 45-60 |

*Results from studies in rhesus monkeys.
**From injection to 95% twitch recovery.

Therefore, the AV001 and AV002 blocking agents have an effective dose that achieves 95% neuromuscular blockage (ED95) of 0.04 mg/kg, whereas AV003, which is the corresponding cis isomer of AV002, has an ED95 of 0.20 mg/kg. A comparison of the trans isomer (AV002) with the cis isomer (AV003) shows that the trans isomer (AV002) is five times more potent. Thus, the trans isomer (AV002) in this series exhibits greater potency and yet has a shorter duration of action (Table 1).

Interestingly, although the structures of these neuromuscular blocking agents are similar, the duration of the blockade caused by these agents differs (Table 1). Thus, the duration of a blockade caused by a 4xED95 dosage of AV001 lasts 50-60 minutes, whereas the blockade caused by a similar dosage of AV002 lasts only 30-35 minutes. The AV003 blocking agent causes paralysis for about 45-60 minutes when administered at a 4xED95 dosage. Thus, small structural changes in the present neuromuscular blocking agents can give rise to significant changes in their biological properties.

EXAMPLE 3

Cysteine and Glutathione Provide Fast Recovery from Neuromuscular Blockade

Rhesus monkeys were anesthetized and treated with a neuromuscular blocking agent as described in Example 1.

FIG. 1 shows how quickly, on average, the five Rhesus monkeys tested (Renoir, Morgan, Soutine, Seurat and Winslow) recovered from administration of the neuromuscular blocking agent AV001, both spontaneously and when a combination of cysteine (20 mg/kg) and glutathione (10 mg/kg) was administered. Spontaneous recovery from AV001 administration took about 2800 seconds (about 46.7 minutes, FIG. 1). However, when a combination of cysteine (20 mg/kg) and glutathione (10 mg/kg) was administered at 2 minutes after AV001 administration, the blockade caused by AV001 was alleviated much faster—in only about 354 seconds (not quite 6 minutes). Therefore, the combination of cysteine and glutathione was a highly effective composition for reversing the effects of the AV001 neuromuscular blocking agent.

Figure 2:
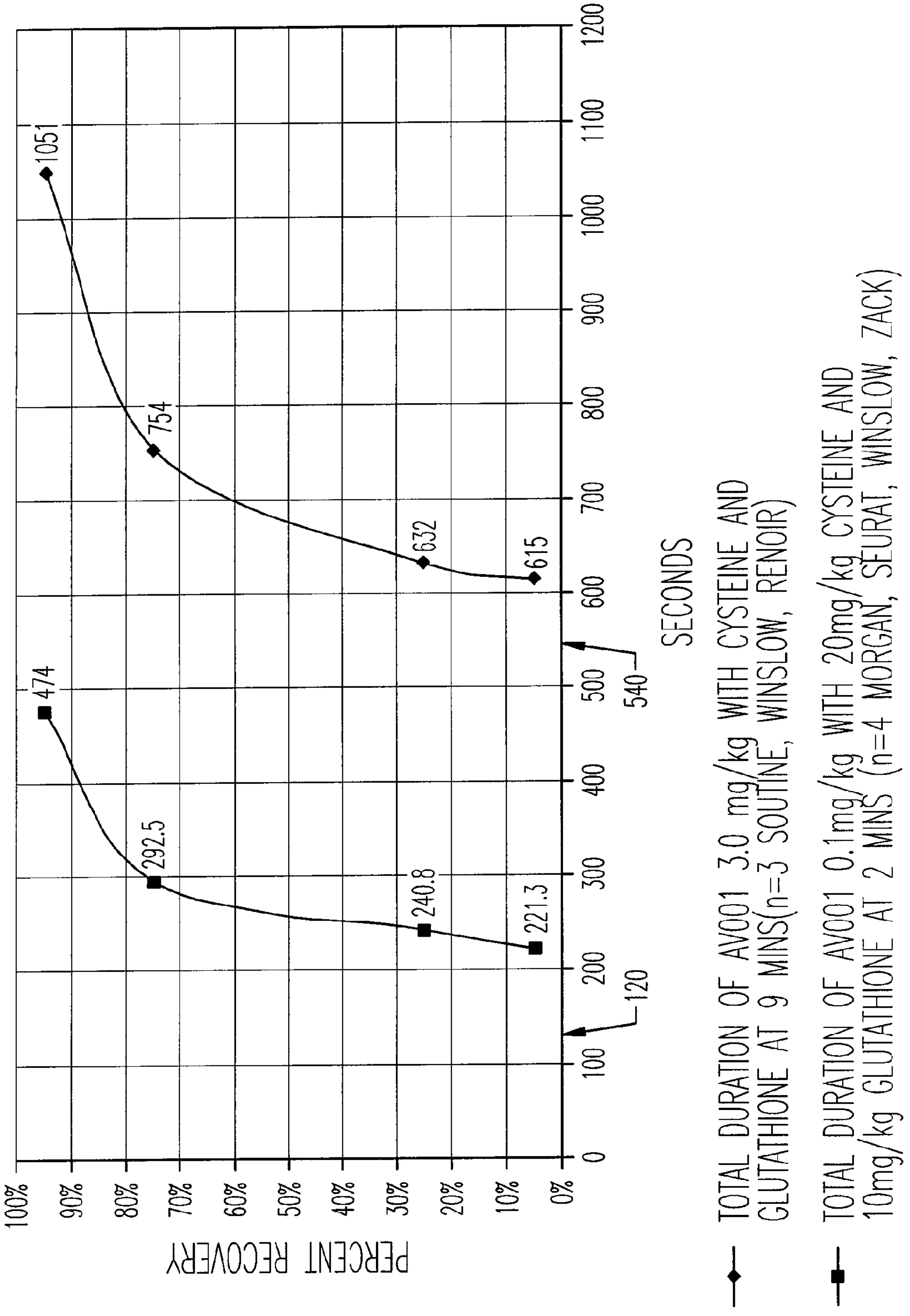
FIG. 2 graphically illustrates the effects of cysteine plus glutathione administration at different times after administering either 0.1 mg/kg or 3.0 mg/kg AV001 neuromuscular blocking agent. When 0.1 mg/kg AV001 (■) is administered and, two minutes later, the blockade is relieved by administration of a combination 20 mg/kg cysteine and 10 mg/kg glutathione, recovery occurs within 354 seconds. However, when a much larger dose of AV001 (3.0 mg/kg, ♦) is administered and, nine minutes later, the blockade is relieved by administration of a combination 20 mg/kg cysteine and 10 mg/kg glutathione, recovery occurs within 511 seconds. Thus, cysteine and glutathione effectively reverse the effects of massive over-doses of AV001.

FIG. 2 shows that the combination of cysteine (20 mg/kg) and glutathione (10 mg/kg) can reverse the effects of a substantial over-dose (30× the effective dose typically used) of AV001. In this study, a normal dosage (0.1 mg/kg) and a massive overdose (3.0 mg/kg) of the AV001 neuromuscular blocking agent were administered to different animals. After two minutes a combination of cysteine (20 mg/kg) and glutathione (10 mg/kg) was administered to the animals who received 0.1 mg/kg AV001, and the neuromuscular blockade was reversed in about 475 seconds, or about 354 seconds after cysteine/glutathione administration. Thus, a normal 0.1 mg/kg dosage of AV001 can be reversed in about 6 minutes. While reversal of the AV001 overdose took about 511 seconds (about 8.5 min.), such reversal was still very fast compared to the overall duration of AV001, particularly when considering that the AV001 was administered at high dosages.

Figure 10:
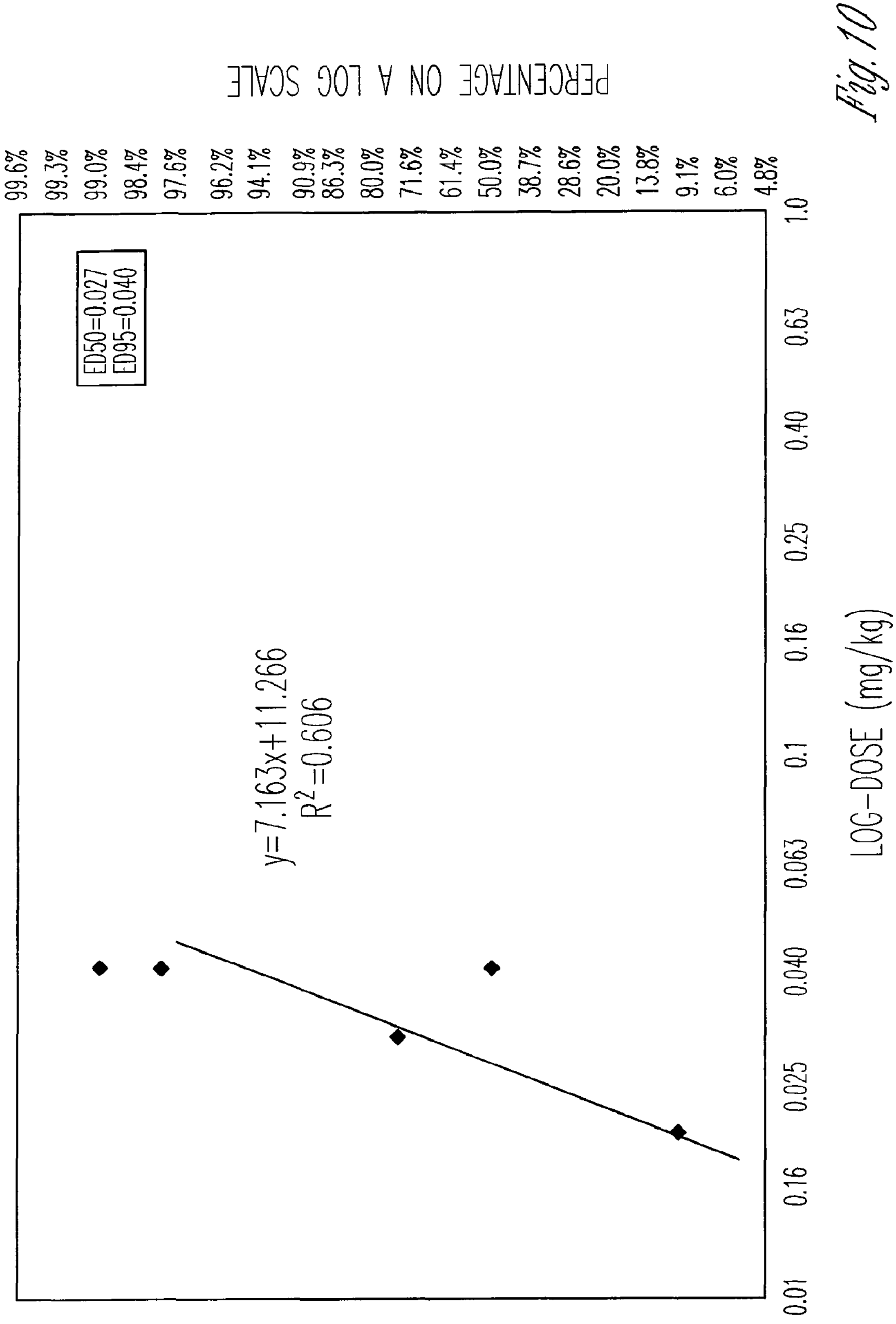
FIG. 10 is a dose-response curve for the AV001 neuromuscular blocking agent plotted on a log scale. As illustrated, the effective dosage for 95% neuromuscular blockade is 0.040 mg/kg and the effective dosage for 50% neuromuscular blockade is 0.027 mg/kg.
Figure 11:
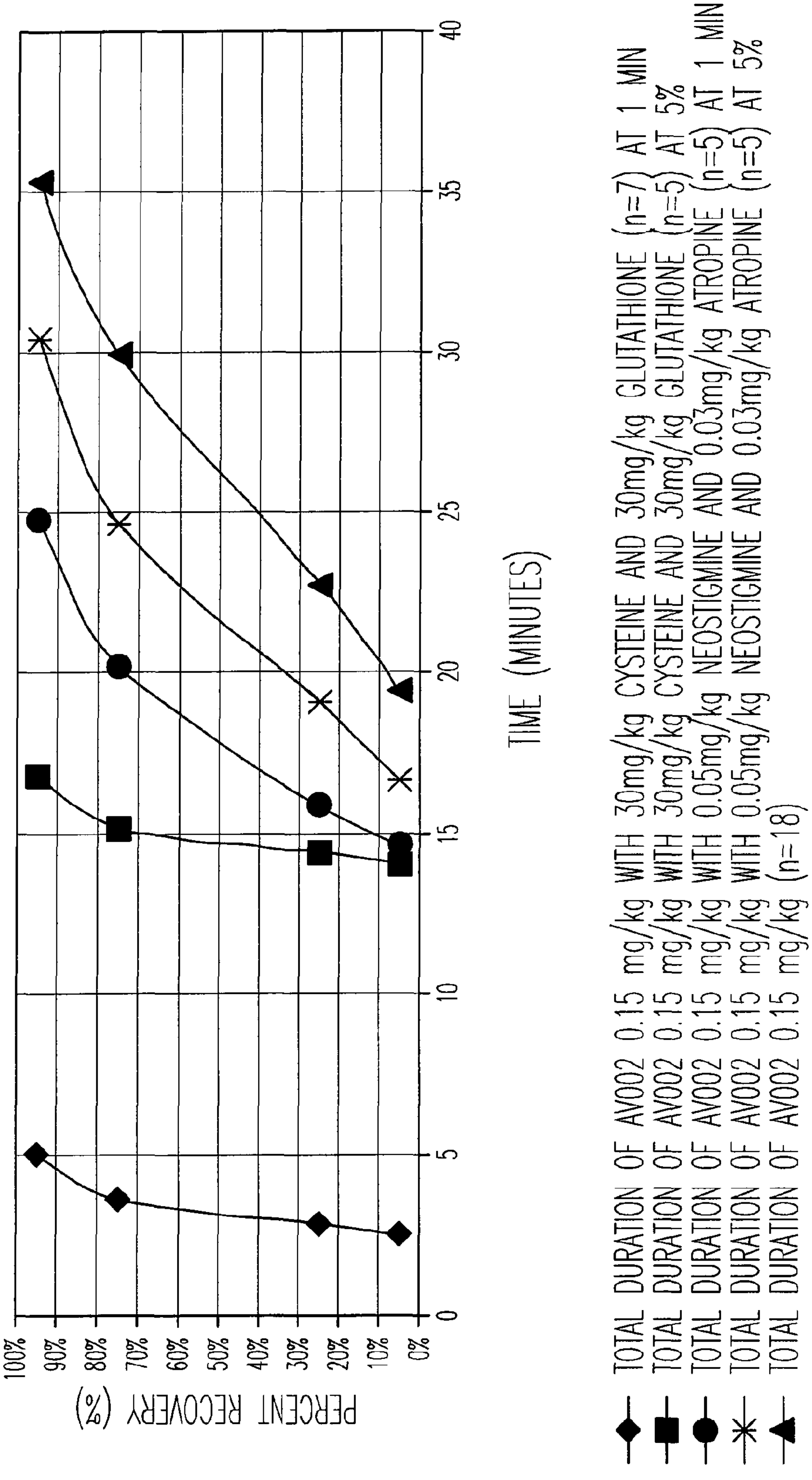
FIG. 11 illustrates recovery times from a neuromuscular blockade caused by AV002 (0.15 mg/kg) by a variety of reversal agents or without (·X·) a reversal agent. Thus, the effect of 30 mg/kg cysteine plus 30 mg/kg glutathione administered at 1 minute (♦) after AV002 administration or at the first sign of twitch recovery (■) is fast, as illustrated. However, traditional reversal agents neostigmine (0.05 mg/kg) and atropine (0.03 mg/kg) administered at 1 minute after AV002 administration (▲) and at first recovery of twitch (●), are slow, as shown.

A dose response curve for AV001 is provided as FIG. 10, illustrating that the effective dose to achieve 95% paralysis for AV001 is 0.040 mg/kg and the effective dose to achieve 50% paralysis is 0.027 mg/kg.

Figure 3:
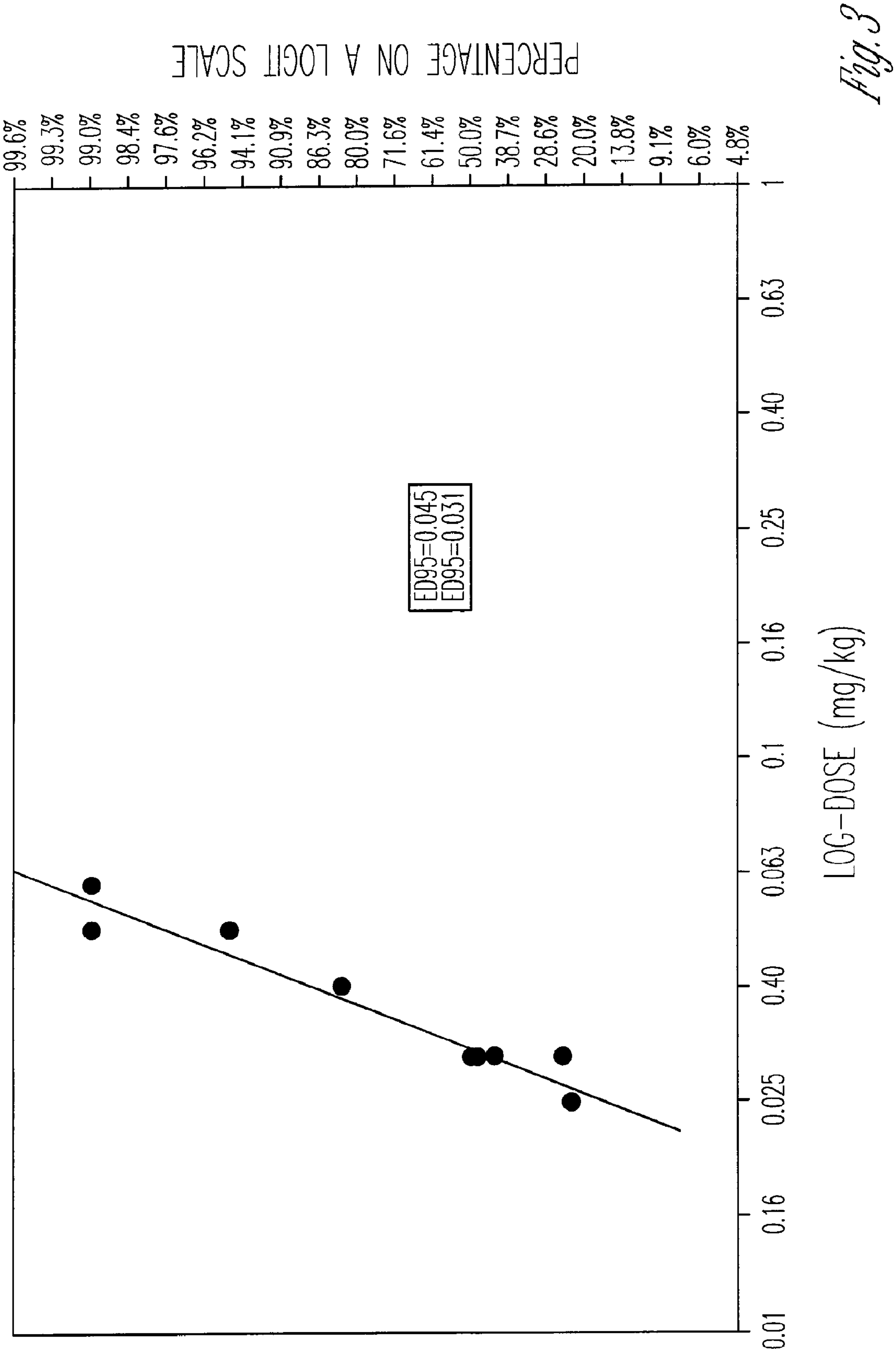
FIG. 3 is a dose-response curve for the AV002 neuromuscular blocking agent plotted using a log scale. As illustrated, the effective dosage for 95% neuromuscular blockade is 0.045 mg/kg and the effective dosage for 50% neuromuscular blockade is 0.031 mg/kg.

FIG. 3 shows a dose response curve for the AV002 neuromuscular blocking agent, demonstrating that fairly small increases in dosage can substantially increase the percent neuromuscular blockade. The effective dose of AV002 to achieve 95% paralysis is 0.045 mg/kg, while the effective AV002 dose to achieve 50% paralysis is 0.031 mg/kg.

Figure 4:
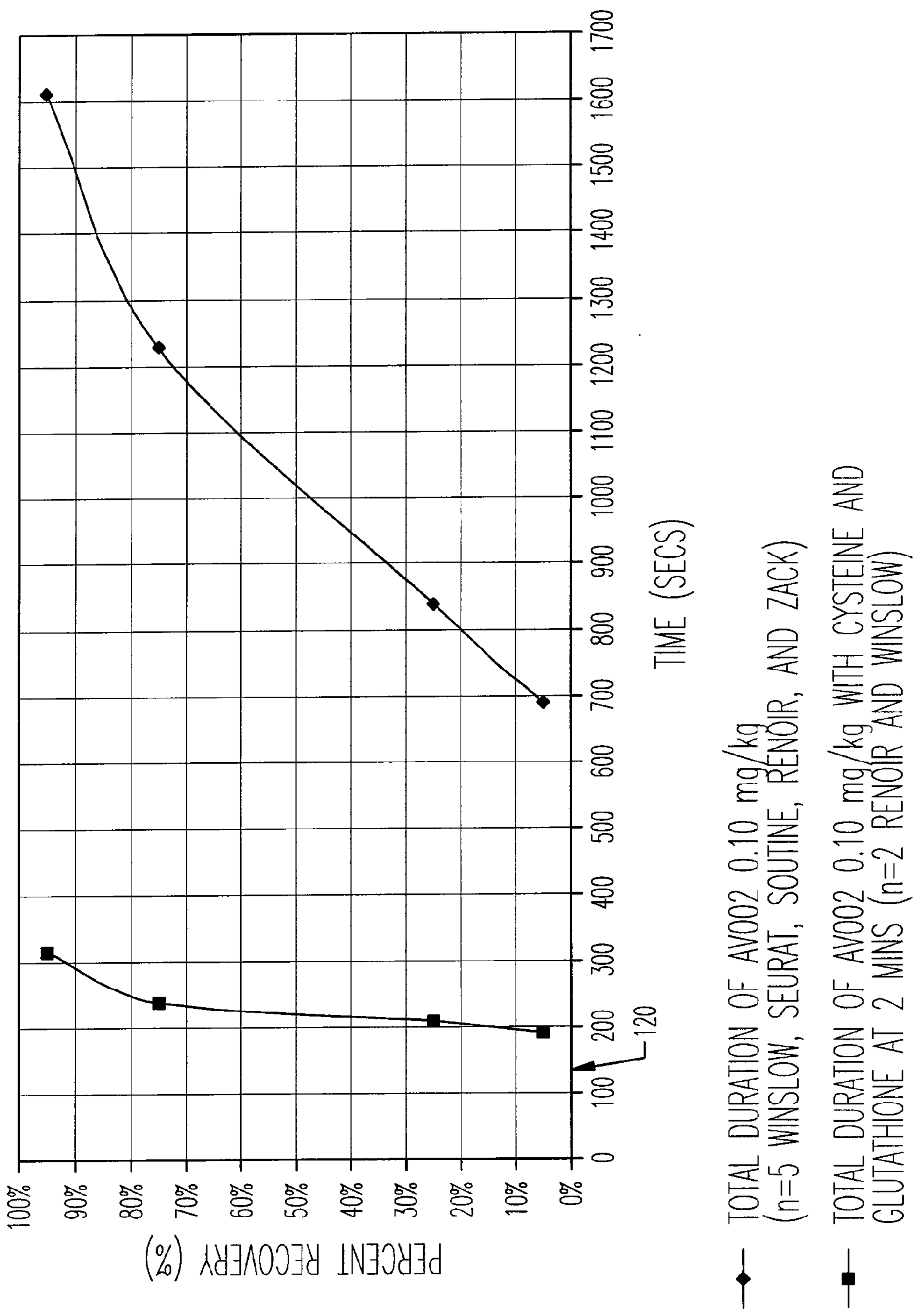
FIG. 4 graphically illustrates the duration of neuromuscular blockade in monkeys caused by administration of 0.1 mg/kg AV002 neuromuscular blocking agent with (■) and without (♦) administration of neuromuscular blockade antagonists (a combination of 20 mg/kg cysteine and 10 mg/kg glutathione). As indicated spontaneous recovery from administration of AV002 takes about 1600 seconds (about 26.6 min.). However, when a combination of cysteine and glutathione is administered at 2 minutes post-administration of AV002, recovery from the neuromuscular blockade takes less than about 200 seconds (about 3 min.).

FIG. 4 illustrates how quickly Rhesus monkeys recovered from administration of 0.1 mg/kg of the AV002 neuromuscular blocking agent, both spontaneously, and when a combination of cysteine (20 mg/kg) and glutathione (10 mg/kg) was administered. Spontaneous recovery from AV002 administration took about 1600 seconds (about 26.7 minutes, FIG. 4). However, when a combination of cysteine (20 mg/kg) and glutathione (10 mg/kg) was administered at 2 minutes after AV002 administration, the blockade caused by AV002 was alleviated much faster—in only about 200 seconds (about 3.3 minutes). Therefore, the combination of cysteine and glutathione was a highly effective composition for reversing the effects of the AV002 neuromuscular blocking agent.

Figure 5:
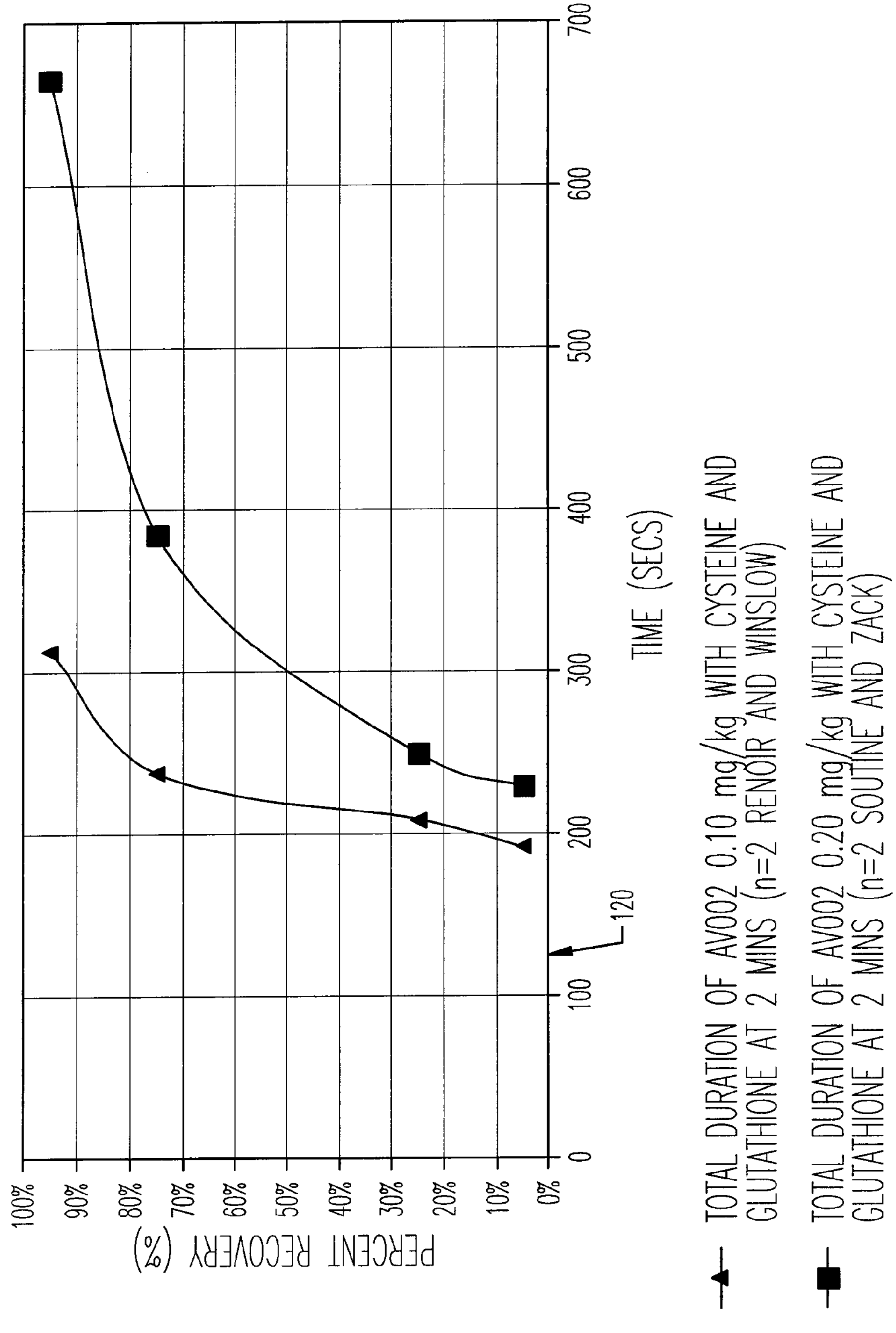
FIG. 5 graphically illustrates the effect of AV002 dosage on the duration of neuromuscular blockade in monkeys after administration of neuromuscular blockade antagonists. When the AV002 dosage is 0.1 mg/kg (▲), reversal of the blockade with a combination of 20 mg/kg cysteine and 10 mg/kg glutathione takes a little less than 200 seconds. However, when the AV002 dosage is 0.2 mg/kg (■), reversal of the blockade with a combination of 20 mg/kg cysteine and 10 mg/kg glutathione takes about 500 seconds.
Figure 6:
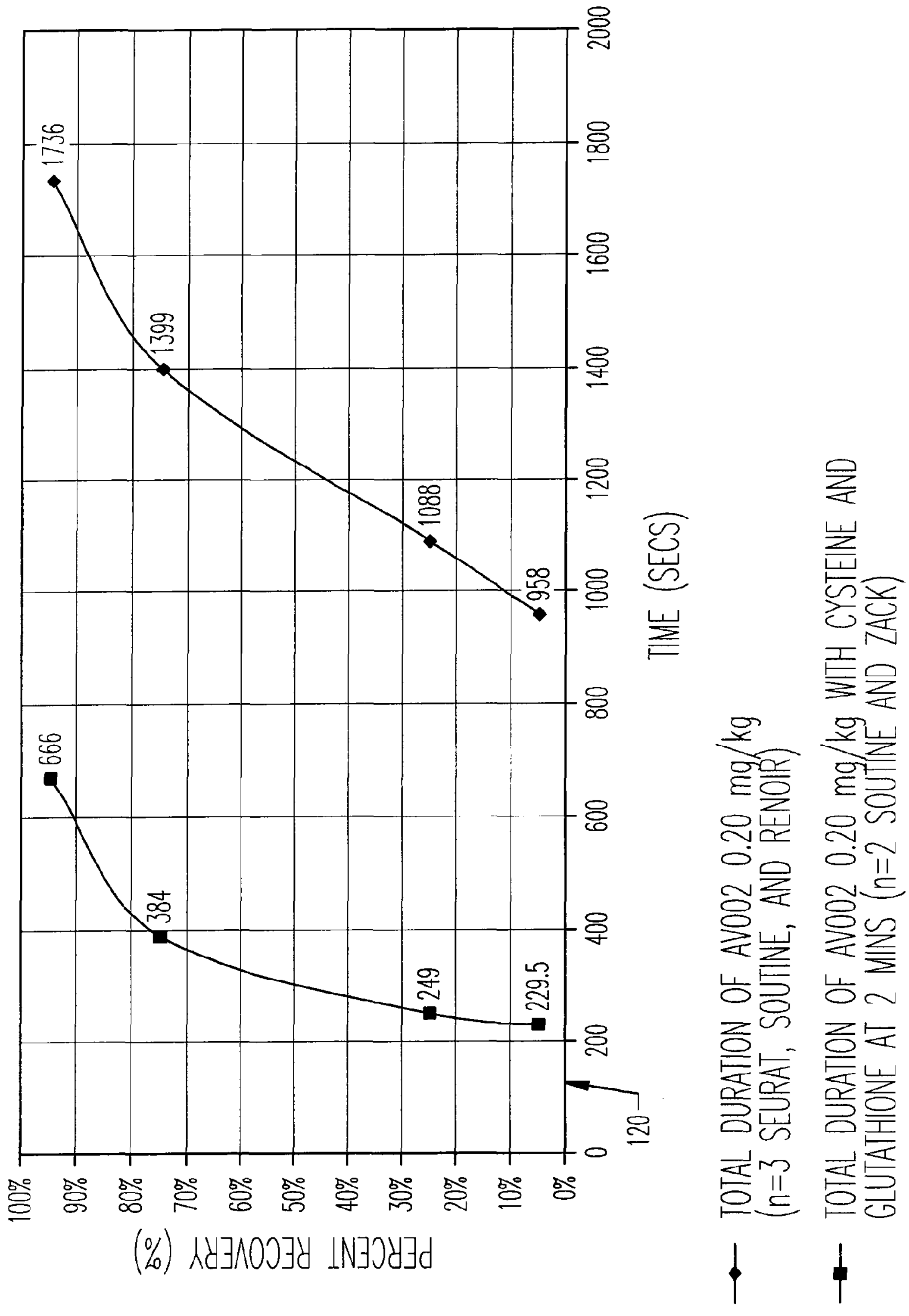
FIG. 6 graphically illustrates the duration of neuromuscular blockade in monkeys caused by administration of 0.2 mg/kg AV002 neuromuscular blocking agent with (■) and without (♦) administration of neuromuscular blockade antagonists (a combination of 20 mg/kg cysteine and 10 mg/kg glutathione). As indicated, spontaneous recovery from administration of AV002 takes about 1730 seconds (about 28.8 min.). However, when a combination of cysteine and glutathione is administered at 2 minutes post-administration of AV002, recovery from the neuromuscular blockade takes less than about 440 seconds (about 7.5 min.).
Figure 7:
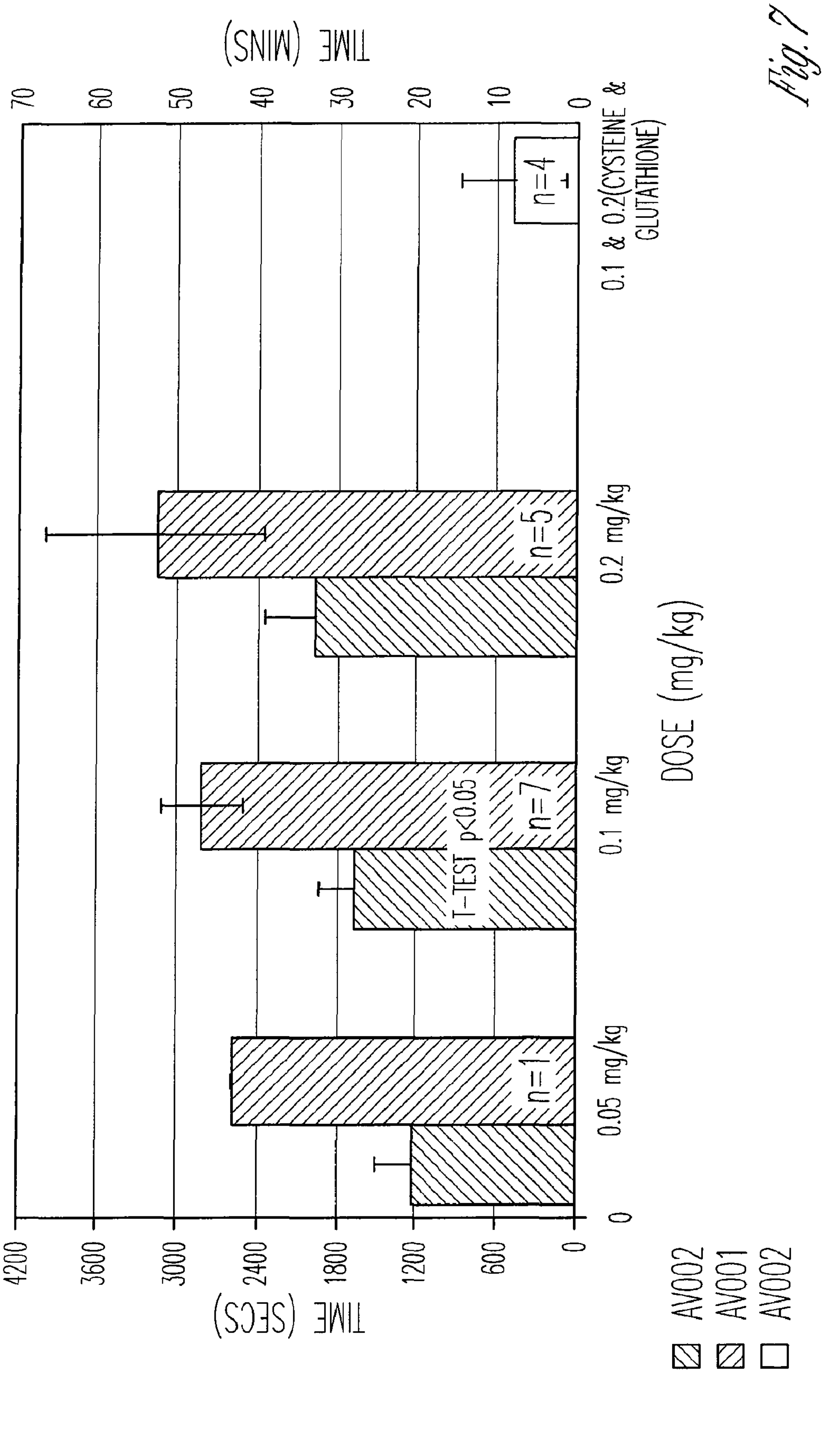
FIG. 7 graphically summarizes the duration of neuromuscular blockade in monkeys caused by administration of the AV001 (bars with \\\) and the AV002 (bars with ///) neuromuscular blocking agents. The bar to the far right without cross-hatching illustrates how administration of an antagonist shortens the duration of the AV002 neuromuscular blockade, where the antagonist used was a combination of cysteine and glutathione.

As shown in FIG. 7, increasing the dosage of AV002 from 0.1 mg/kg to 0.2 mg/kg increases the duration of the neuromuscular blockade from about 1766 seconds to about 2150 seconds. Thus, modulation of the dosage of AV002 can be used to modulate the duration of an AV002-induced neuromuscular blockade. As shown in FIG. 5, use of a combination of cysteine and glutathione quickly reversed the effects of the AV002 blockade. However, increasing the dosage of AV002 from 0.1 mg/kg to 0.2 mg/kg increased the time for reversal of the neuromuscular blockade from about 320 seconds to about 670 seconds. None-the-less, the 670 second reversal time for a higher dosage of AV002 substantially reduced the time for recovery from about 2150 seconds to about 670 seconds. Thus, the combination of cysteine and glutathione is a highly effective neuromuscular blockade reversal composition.

FIG. 7 graphically summarizes and compares the duration of AV001 and AV002 blocking agents.

EXAMPLE 4

Figure 8:
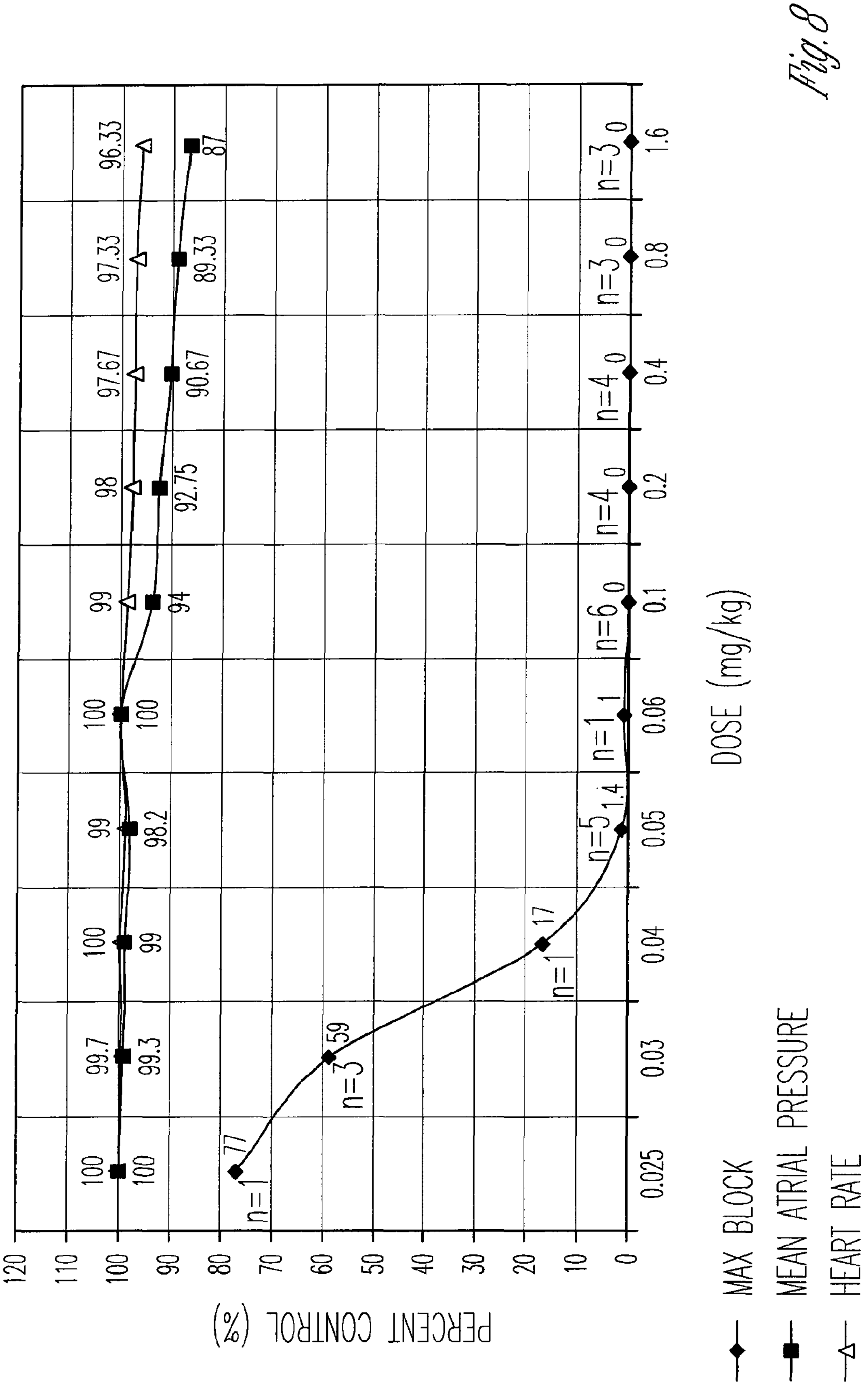
FIG. 8 graphically summarizes the mean arterial blood pressure (■), the heart rate (Δ) and the maximal block (♦) observed for increasing dosages of the AV002 neuromuscular blocking agent.
Figure 9:
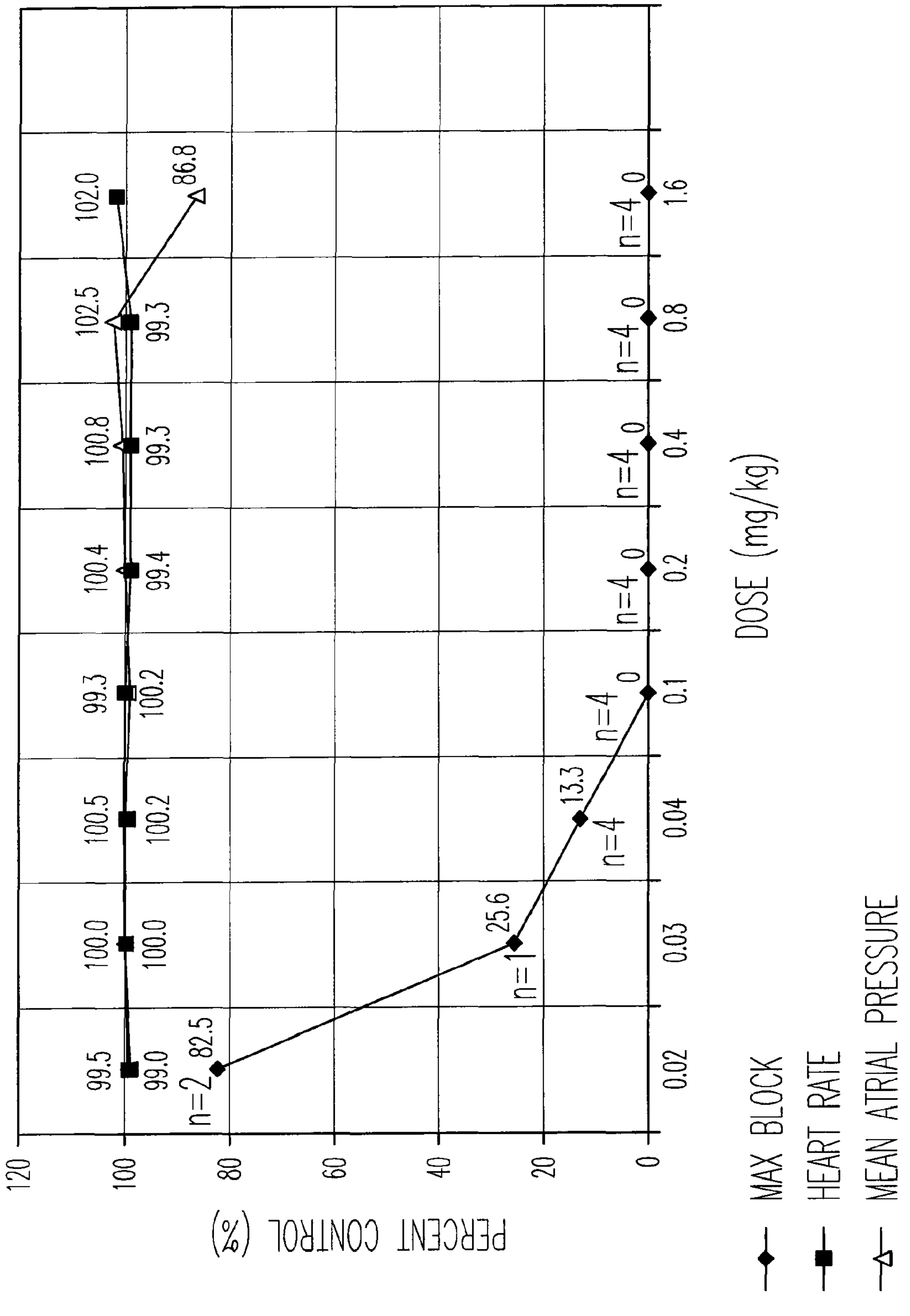
FIG. 9 graphically summarizes the mean arterial blood pressure (Δ), the heart rate (■) and the maximal block (♦) observed for increasing dosages of the AV001 neuromuscular blocking agent.

Neuromuscular Blocking Agents and Antagonist Administration have Essentially No Side Effects Rhesus monkeys were anesthetized and treated with a neuromuscular blocking agent as described in Example 1. FIGS. 8 and 9 provide mean values for the cardiovascular effects of administration of the AV002 and AV001 neuromuscular blocking agents, respectively as a function of dosage.

FIG. 8 graphically illustrates that little or no change occurs in the mean arterial pressure (■) and heart rate (▲) of animals receiving even high dosages of AV002. Similarly, FIG. 9 graphically illustrates that little or no change occurs in the mean arterial pressure (▲) and heart rate (■) of animals receiving high dosages of AV001. Thus, the AV001 and AV002 neuromuscular blocking agents exhibit no signs of causing physiological distress to the circulation in vivo.

EXAMPLE 5

Reversal of the AV002 Neuromuscular Blocking Agent Using Cysteine, Glutathione, Neostigmine and Atropine This Example illustrates the spontaneous recovery from treatment with AV002 as compared to recovery from AV002 treatment accelerated by cysteine and glutathione. In addition, the Example illustrates recovery from AV002 treatment using the conventional reversal agents, neostigmine and atropine.

Methods

Anesthesia was induced in adult male rhesus monkeys using 7.5 mg/kg ketamine. Tracheae were intubated using topical anesthetic. Anesthesia was maintained with isoflurane 1-2% and $N_2O/O_2$ (60%/40%). ECG, temperature, $O_2$ saturation, and blood pressure were monitored and maintained within normal limits. Mechanomyogram (MMG) recordings were made of twitch responses from the extensor digitorum at 0.15 Hz. A control dose of AV002 (0.15 mg/kg; about 3 times the $ED_{95}$) was given and animals were allowed to recover spontaneously. Another dose of 0.15 mg/kg of AV002 was given approximately 30 minutes after return of train of four (TOF) to greater than 100%. Reversal of the second dose of AV002 was attempted in four separate groups of animals with either:

1) cysteine 30 mg/kg and glutathione 30 mg/kg at 1 minute after injection of AV002, 2) cysteine 30 mg/kg and glutathione 30 mg/kg at the first sign of recovery of twitch, 3) neostigmine 0.05 mg/kg and atropine 0.03 mg/kg at 1 minute after injection of AV002, or 4) neostigmine 0.05 mg/kg and atropine 0.03 mg/kg at the first sign of recovery of twitch.

Comparative recovery intervals and total duration were analyzed using the student t-test.

Results

A dosage of AV002 equivalent to approximately three times the ED95 dosage was most effectively reversed when a combination of cysteine and glutathione was used. Thus, injection of cysteine and glutathione one minute following AV002 injection decreased the average total duration of neuromuscular blockade by 27.24 minutes ($p=<0.0001$). Neostigmine and atropine administration at 1 minute following AV002 injection had no effect on the duration of the neuromuscular blockade ($p=0.11$). Cysteine and glutathione administration at first twitch (a sign of recovery) decreased the average recovery interval by 6.81 minutes compared to administration of neostigmine and atropine at first twitch recovery ($p=0.03$).

TABLE 2

| Comparison of Reversal Agents<br>Reversal of AV002 0.15 mg/kg (3XED95) | | | |
|---|---|---|---|
| Reversal | n | Total Duration (inj − 95%) (minutes ± SE) | Recovery Interval (5-95%) (minutes ± SE) |
| Spontaneous | 18 | 30.45 ± 2.24 | 13.78 ± 1.27 |
| Cysteine/Glutathione at 1 minute | 7 | 5.04 ± 0.88 | 2.50 ± 0.73 |
| Neostigmine/Atropine at 1 minute | 5 | 35.33 ± 6.69 | 15.87 ± 3.08 |
| Cysteine/Glutathione at first recovery of twitch | 5 | 16.85 ± 1.63 | 2.78 ± 0.29 |
| Neostigmine/Atropine at first recovery of twitch | 5 | 24.81 ± 6.82 | 10.11 ± 3.03 |

AV002 is an intermediate-acting nondepolarizing neuromuscular blocker. Exogenous cysteine and glutathione will reverse neuromuscular block in approximately 3 minutes, even when a dosage of three times the $ED_{95}$ dose of AV002 is administered. The 3 minute recovery period was observed when the cysteine and glutathione were given 1 minute following drug injection and at the first sign of twitch recovery. By comparison, traditional reversal with neostigmine was achieved in approximately 10 minutes when neostigmine is given at the first sign of twitch recovery and has no effect on the duration when given one minute after AV002 injection.

The combination of rapid onset, potential for immediate reversal after an intubation dose, and intermediate duration with a wide circulatory safety ratio indicates that AV002 is a useful neuromuscular blocker that may be used in clinical practice.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A neuromuscular blocking agent selected from the group consisting of:

AV001

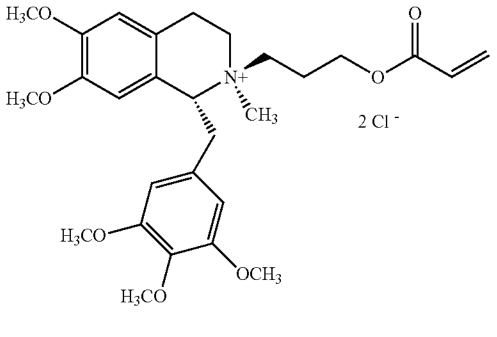

-continued
AV002
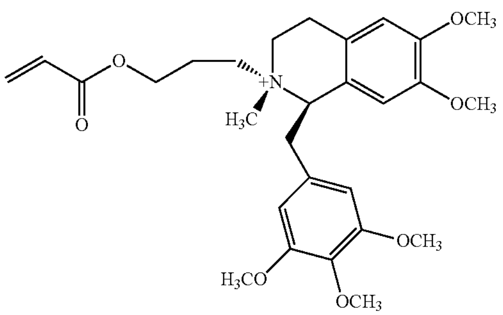
AV003
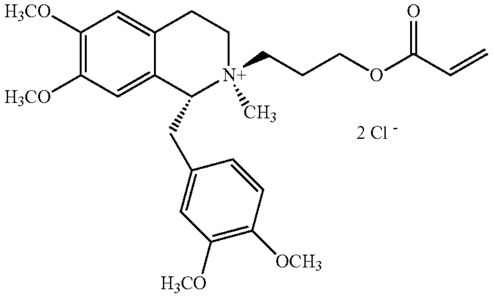
AV004
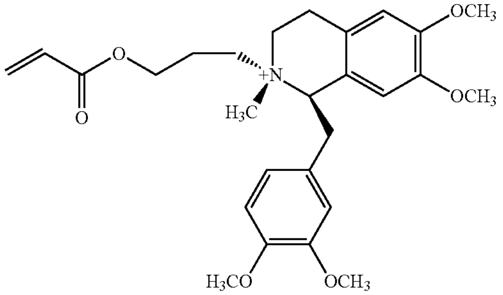
-continued
AV005
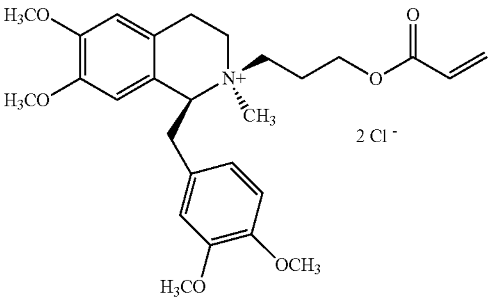
AV006
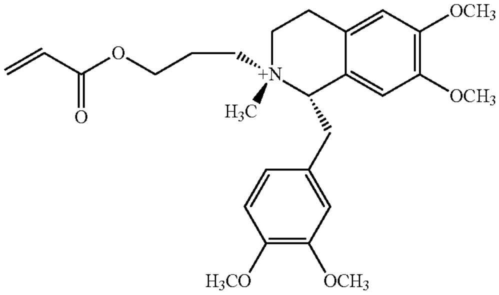
and combinations thereof.
2. A composition comprising a pharmaceutically acceptable carrier and an amount of a neuromuscular blocking agent sufficient to paralyze a mammalian subject, wherein the neuromuscular blocking agent is selected from the group consisting of:
AV001
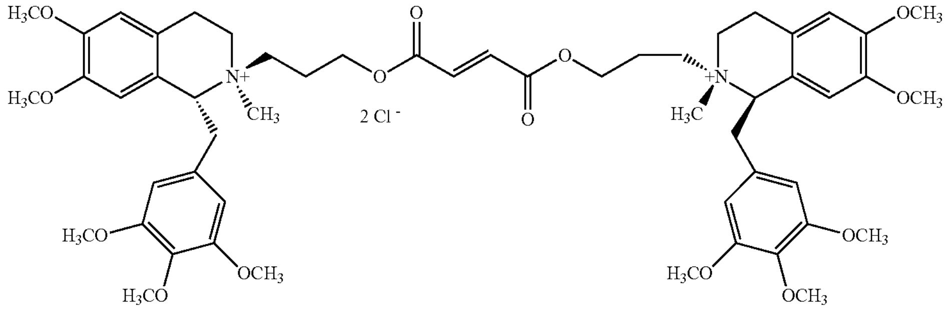

-continued

AV002

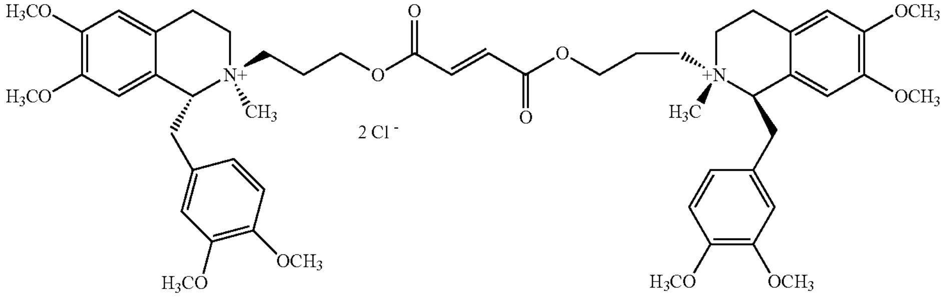

AV003

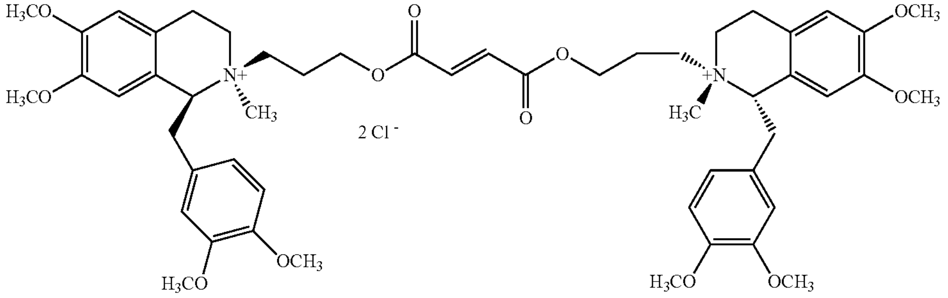

and a combination thereof.

3. The composition of claim 2, wherein the neuromuscular blocking agent has the following structure:

AV002

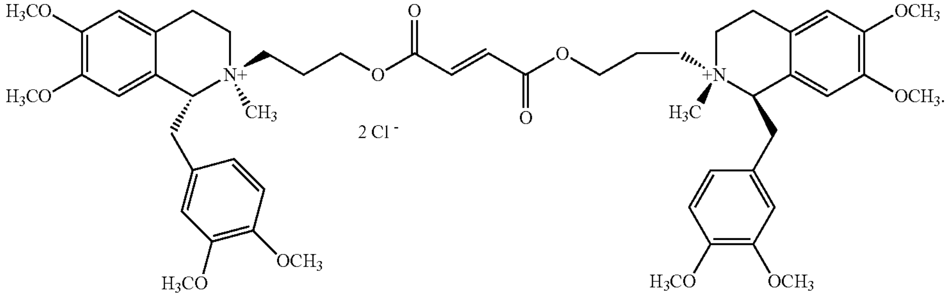

4. A method of inducing a neuromuscular blockade in a mammal comprising administering to the mammal a composition comprising an amount of a neuromuscular blocking agent sufficient to paralyze the mammal, wherein the neuromuscular blocking agent is selected from the group consisting of:

AV001

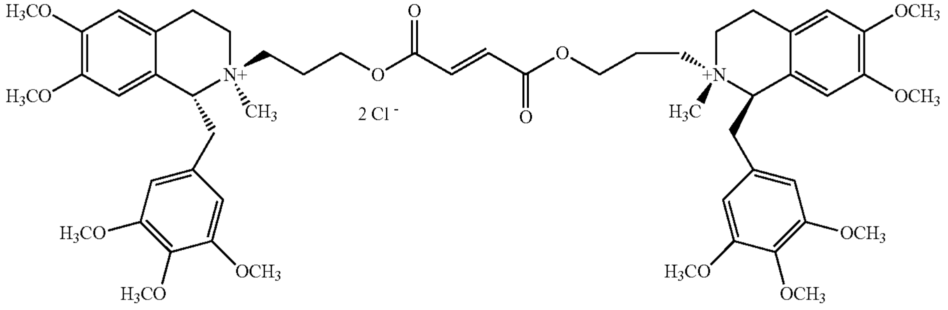

-continued

AV002

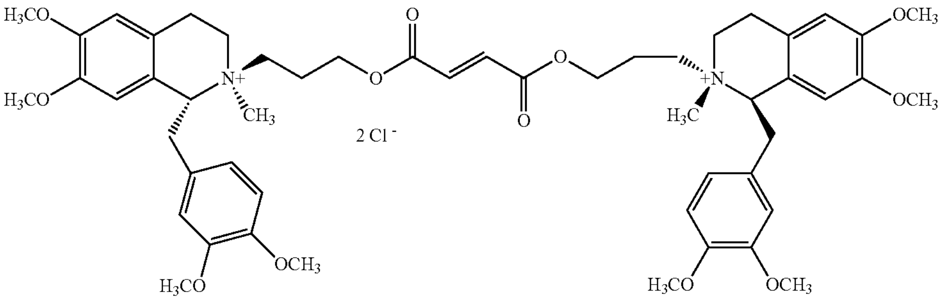

AV003

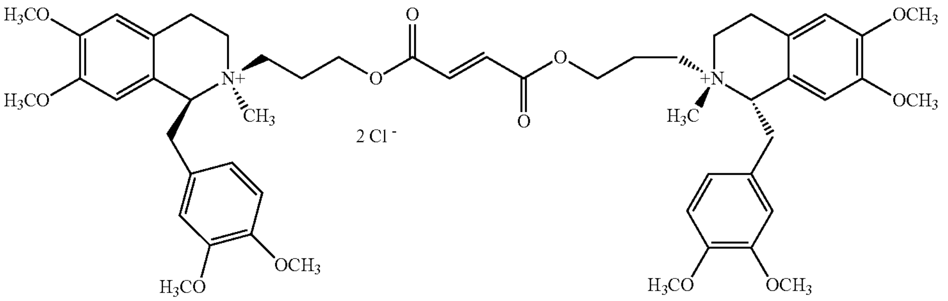

and a combination thereof.

5. The method of claim 4, wherein the neuromuscular blocking agent has the following structure:

AV002

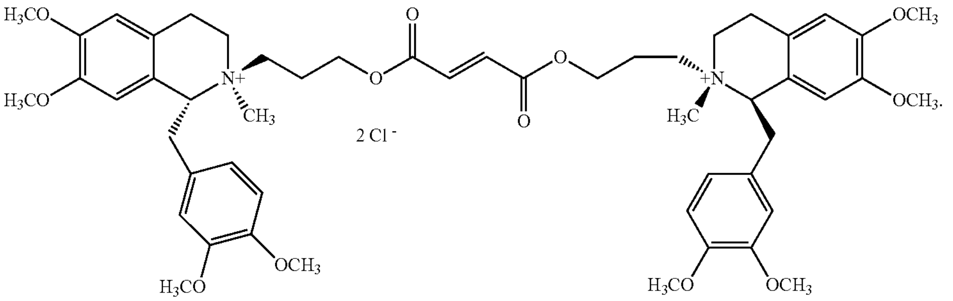

6. The method of claim 4, wherein the mammal is also subjected to general anesthesia.

7. The method of claim 4, wherein the neuromuscular blocking agent is administered in an amount effective to paralyze the mammal.

8. The method of claim 4, wherein the mammal is a human.

9. A method of reversing a neuromuscular blockade in a mammal comprising administering to the mammal an effective amount of cysteine, N-acetylcysteine, glutathione, homocysteine, methionine, S-adenosyl-methionine, penicillamine, a combination thereof or a pharmaceutically acceptable salt thereof, wherein the neuromuscular blockade is generated by the method comprising inducing a neuromuscular blockade in a mammal by administering to the mammal a composition comprising an amount of a neuromuscular blocking agent sufficient to paralyze the mammal, wherein the neuromuscular blocking agent is selected from the group consisting of:

AV001

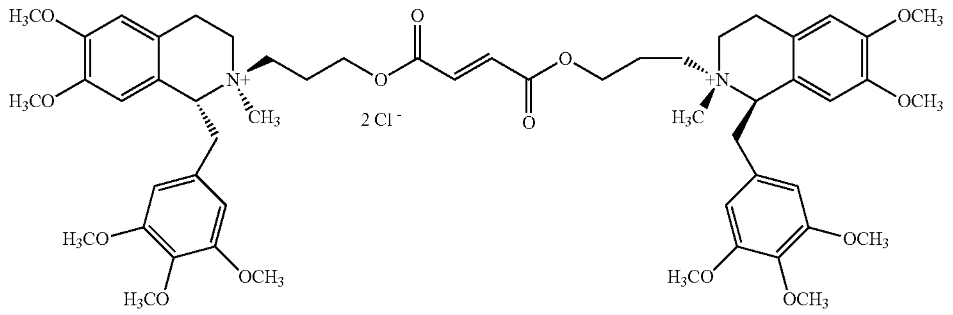

AV002

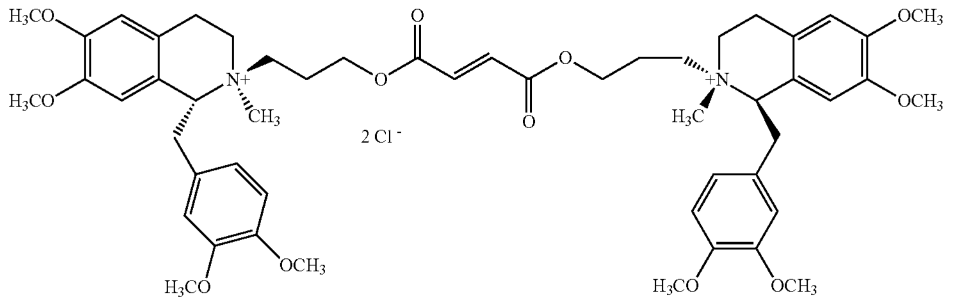

AV003

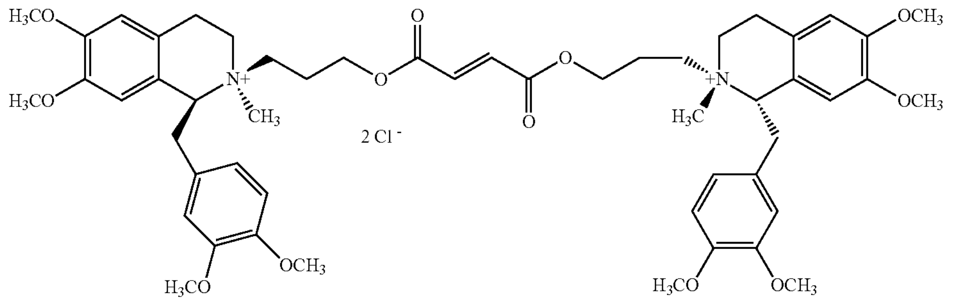

and a combination thereof.

10. The method of claim 9, wherein cysteine is administered.

11. The method of claim 9, wherein glutathione is administered.

12. The method of claim 9, wherein a combination of cysteine and glutathione are administered.

13. The method of claim 9, wherein the cysteine, N-acetylcysteine, glutathione, homocysteine, methionine, S-adenosyl-methionine, penicillamine, a combination thereof or a pharmaceutically acceptable salt thereof, are administered intravenously, in combination with a pharmaceutically acceptable liquid carrier.

14. The method of claim 9, wherein the cysteine, N-acetylcysteine, glutathione, homocysteine, methionine, S-adenosyl-methionine, penicillamine, a combination thereof or a pharmaceutically acceptable salt thereof, are administered in a dosage of about 0.1 mg/kg to about 500 mg/kg.

15. The method of claim 9, wherein the mammal is a domestic or zoo animal.

16. The method of claim 9, wherein the mammal is a human.

17. A kit comprising, separately packaged, (a) an effective amount of a neuromuscular blocking agent selected from the group consisting of:

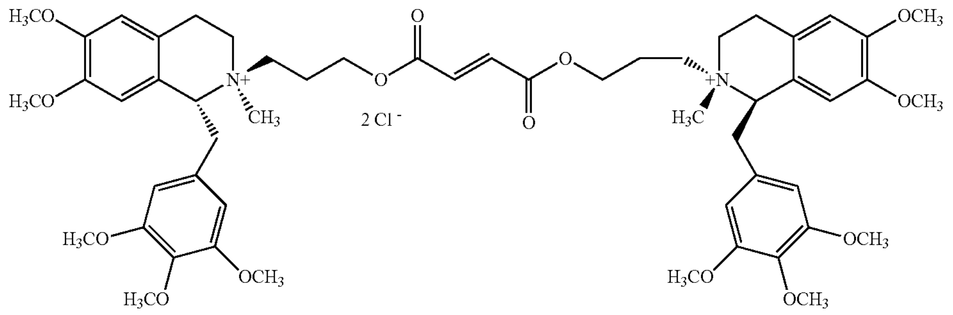

AV001

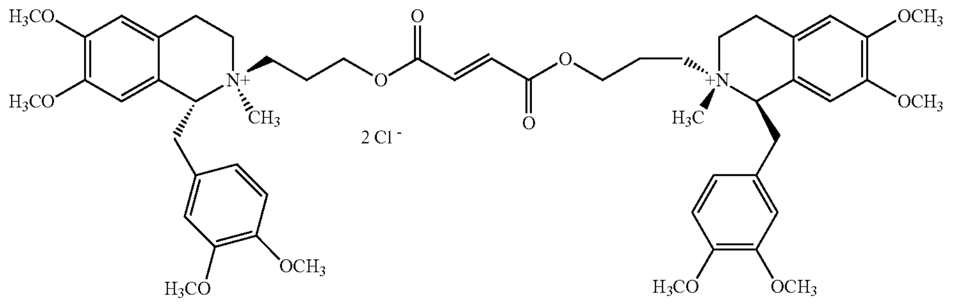

AV002

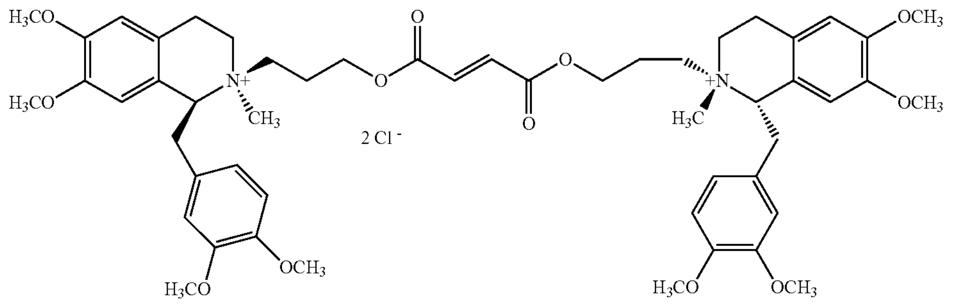

AV003 and combinations thereof, (b) an effective amount of an antagonist to the neuromuscular blocking agent, and (c) instructions directing the user to employ the antagonist to reverse the effects of the blocking agent on a mammal to which the blocking agent is administered; wherein the antagonist is cysteine, N-acetylcysteine, glutathione, homocysteine, methionine, S-adenosyl-methionine, penicillamine, a combination thereof, or a pharmaceutically acceptable salt thereof.

18. The kit of claim 17, wherein the neuromuscular blocking agent is formulated to be administered intravenously, in combination with a pharmaceutically acceptable liquid carrier.

19. The kit of claim 17, wherein the antagonist is formulated to be administered intravenously, in combination with a pharmaceutically acceptable liquid carrier.

20. The kit of claim 17, wherein the antagonist is cysteine, glutathione, a combination thereof or a pharmaceutically acceptable salt thereof.

21. The kit of claim 17, wherein the antagonist is a combination of cysteine and glutathione.

22. The kit of claim 17, wherein the neuromuscular blocking agent has the following structure:
AV002
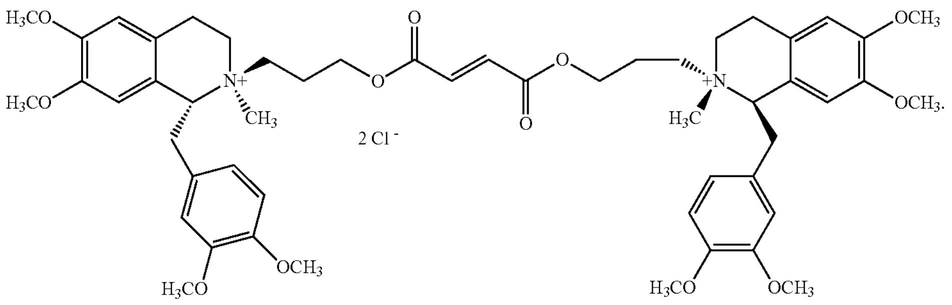
* * * * *

UNITED STATES PATENT AND TRADEMARK OFFICE

CERTIFICATE OF CORRECTION

PATENT NO. : 8,148,398 B2
APPLICATION NO. : 11/951114
DATED : April 3, 2012
INVENTOR(S) : John J. Savarese It is certified that error appears in the above-identified patent and that said Letters Patent is hereby corrected as shown below:

ON THE TITLE PAGE:

On page 2, Item (56) under “Other Publications”, in column 1, line 17, delete “Unusal” and insert -- Unusual --, therefor.

On page 2, Item (56) under “Other Publications”, in column 1, line 36, delete “Anaesthology” and insert -- Anesthesiology --, therefor.

On page 2, Item (56) under “Other Publications”, in column 1, line 58, delete “Produgs” and insert -- Prodrugs --, therefor.

On page 2, Item (56) under “Other Publications”, in column 1, line 66, delete “Cuurent” and insert -- Current --, therefor.

Signed and Sealed this
Twenty-third Day of October, 2012

David J. Kappos
*Director of the United States Patent and Trademark Office*

In Claim 1, delete:
AV001
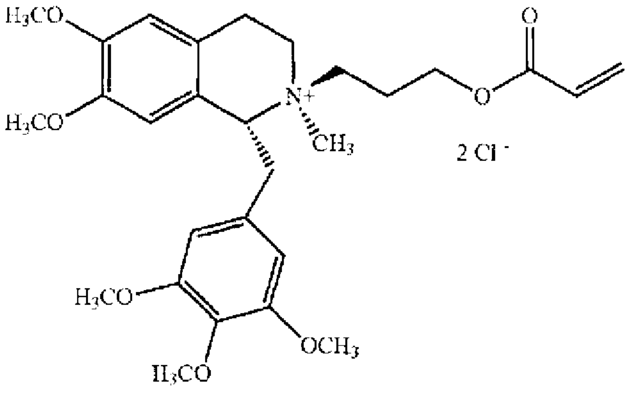
AV002
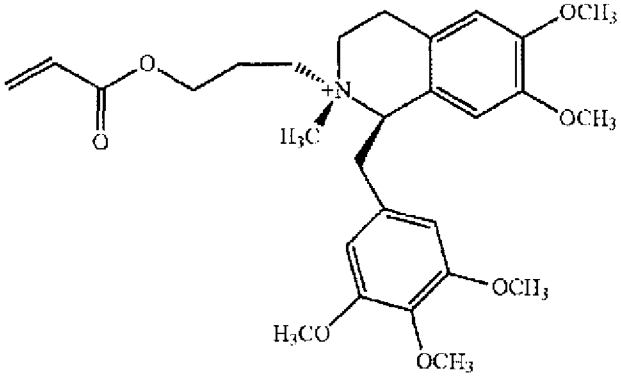
“

AV003
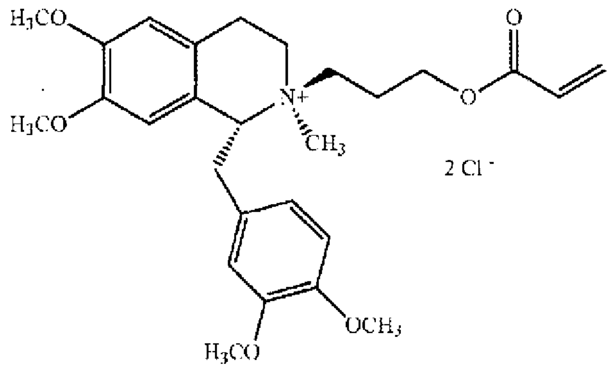
AV004
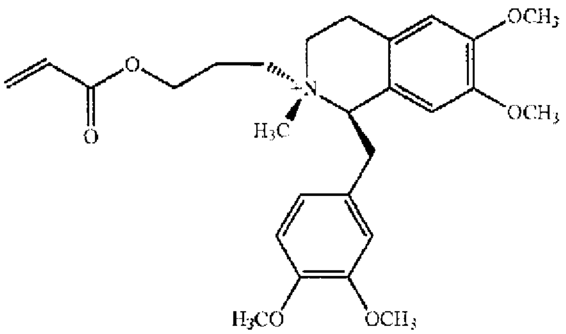

AV005
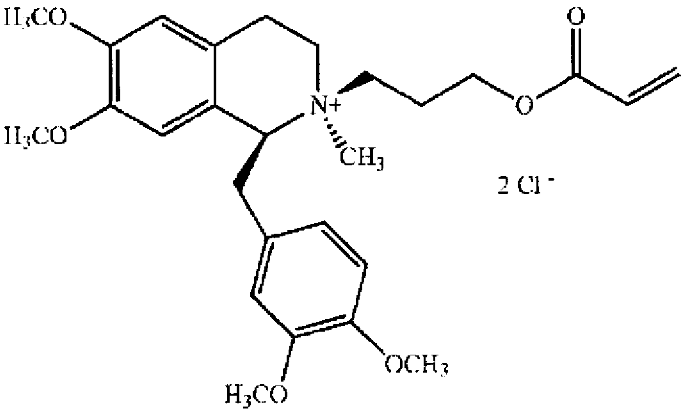
AV006
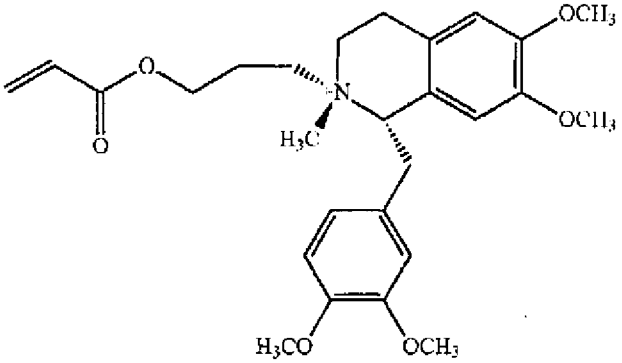
"

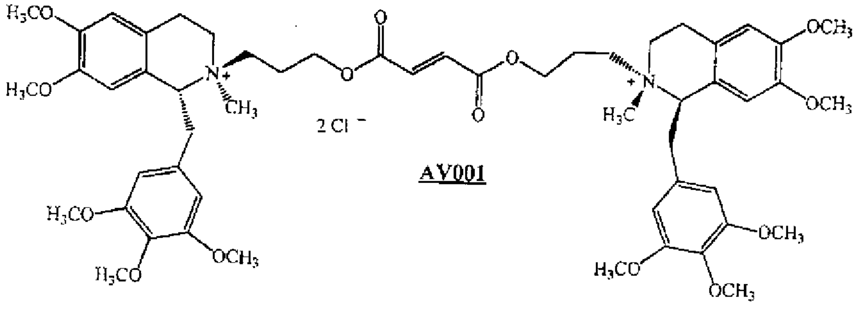
AV001
and insert --
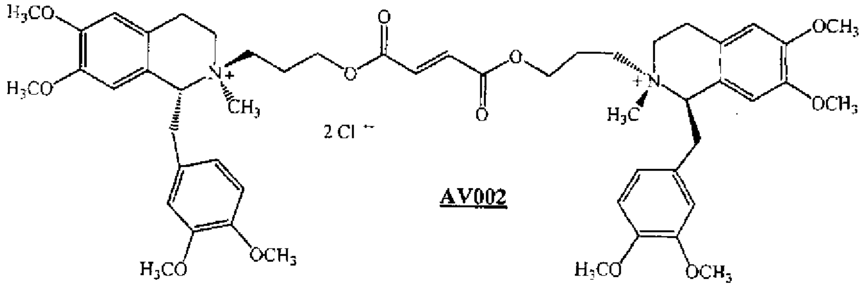
AV002
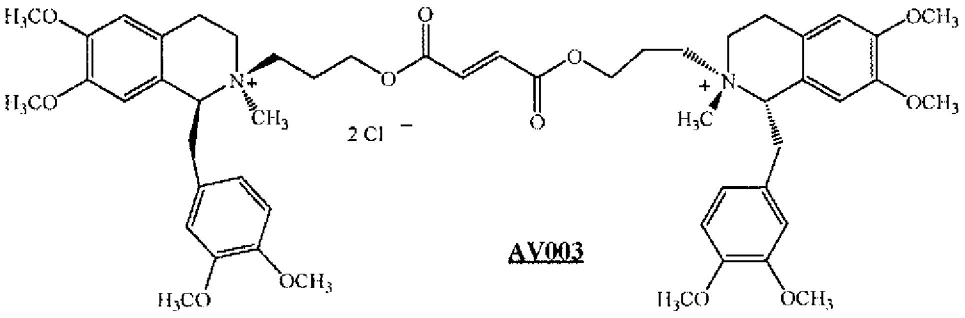
AV003
--, therefor.